United States Patent
Daley, II et al.

(10) Patent No.: US 12,082,903 B2
(45) Date of Patent: Sep. 10, 2024

(54) DRAPE FOR AN IMAGING SYSTEM GANTRY

(71) Applicant: InSurgery, LLC, Lunenburg, MA (US)

(72) Inventors: Edward J. Daley, II, Maynard, MA (US); Russell Stanton, Lunenburg, MA (US)

(73) Assignee: InSurgery, LLC, Lunenburg, MA (US)

( * ) Notice: Subject to any disclaimer, the term of this patent is extended or adjusted under 35 U.S.C. 154(b) by 367 days.

(21) Appl. No.: 17/666,016

(22) Filed: Feb. 7, 2022

(65) Prior Publication Data
US 2022/0323169 A1  Oct. 13, 2022

Related U.S. Application Data

(60) Provisional application No. 63/173,689, filed on Apr. 12, 2021.

(51) Int. Cl.
*A61B 46/10* (2016.01)
*A61B 6/00* (2024.01)

(52) U.S. Cl.
CPC ............ *A61B 46/10* (2016.02); *A61B 6/4423* (2013.01)

(58) Field of Classification Search
CPC ........ A61B 46/10; A61B 6/032; A61B 6/4423
See application file for complete search history.

(56) References Cited

U.S. PATENT DOCUMENTS

| | | | | |
|---|---|---|---|---|
| 4,910,819 A | * | 3/1990 | Brown ................... | A61B 46/10 5/482 |
| 6,123,080 A | * | 9/2000 | Mohan ................... | A61B 46/10 128/849 |
| 2005/0213712 A1 | * | 9/2005 | Cadwalader ......... | A61B 6/4423 378/203 |
| 2005/0213713 A1 | * | 9/2005 | Cadwalader ......... | A61B 6/4423 378/203 |
| 2008/0216844 A1 | * | 9/2008 | Olfert ..................... | A61B 46/10 128/856 |
| 2011/0297164 A1 | * | 12/2011 | Strauch ................. | A61B 46/40 128/849 |
| 2012/0237000 A1 | * | 9/2012 | Rahme .................... | A61B 6/10 378/204 |
| 2013/0025605 A1 | * | 1/2013 | Ball ....................... | A61B 46/10 128/849 |

(Continued)

FOREIGN PATENT DOCUMENTS

EP    1262146 A2    12/2012

OTHER PUBLICATIONS

Written Opinion of the International Searching Authority, mailed May 23, 2022 for International Application No. PCT/US2022/015594, 6 pgs.

*Primary Examiner* — Dani Fox
*Assistant Examiner* — Soorena Kefayati
(74) *Attorney, Agent, or Firm* — Iandiorio Teska & Coleman, LLP

(57) ABSTRACT

An imaging system drape includes leaves for easier deployment. A gantry first outer side wall covering portion includes a top leaf and one or more adjacent leaves on opposite sides of the top leaf. There is a stay for each leaf, a gantry inner wall covering portion extending from the gantry first outer side wall covering portion, and one or more drape portions attached to the gantry inner wall covering portion and securable to a gantry second outer side wall.

27 Claims, 27 Drawing Sheets

(56) References Cited

U.S. PATENT DOCUMENTS

| | | | |
|---|---|---|---|
| 2013/0092177 A1* | 4/2013 | Chua | A61B 5/055 |
| | | | 53/429 |
| 2015/0038835 A1* | 2/2015 | Murphy | A61B 6/032 |
| | | | 600/567 |
| 2015/0114404 A1* | 4/2015 | Czop | A61B 46/10 |
| | | | 128/856 |
| 2020/0054299 A1* | 2/2020 | Daley, II | A61B 6/547 |

* cited by examiner

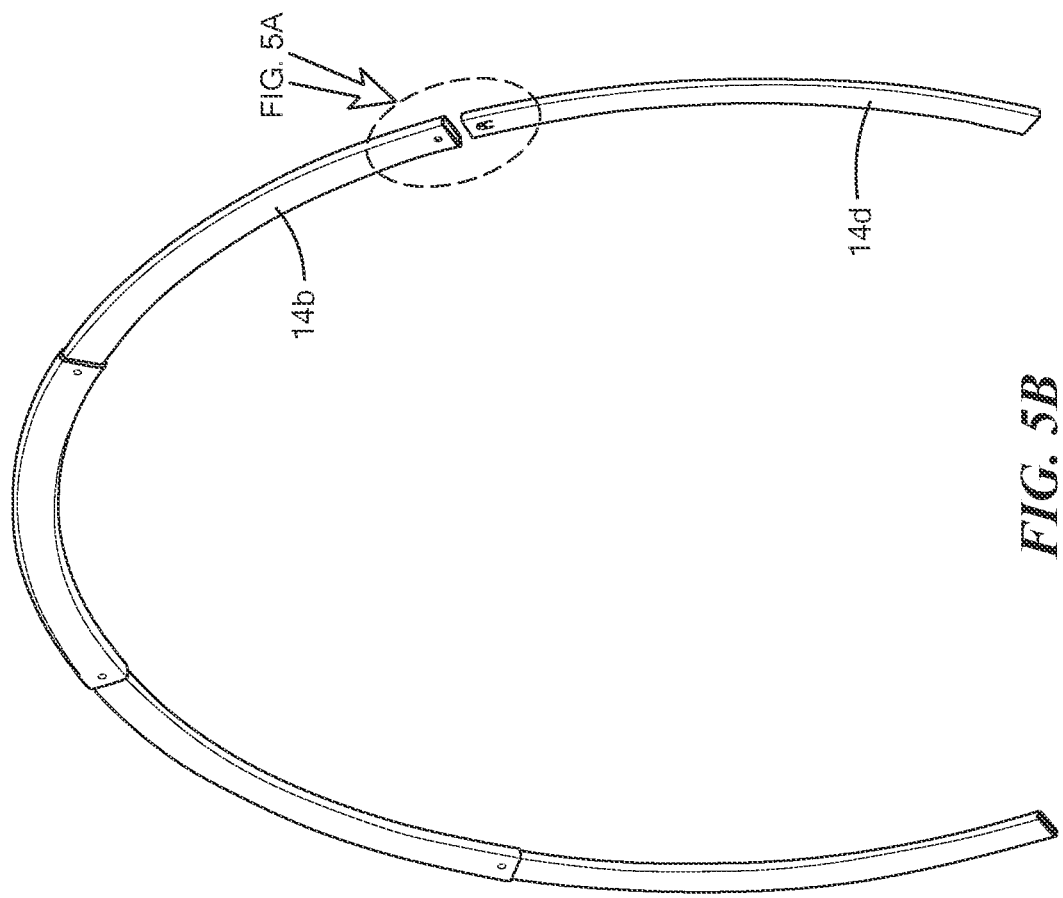
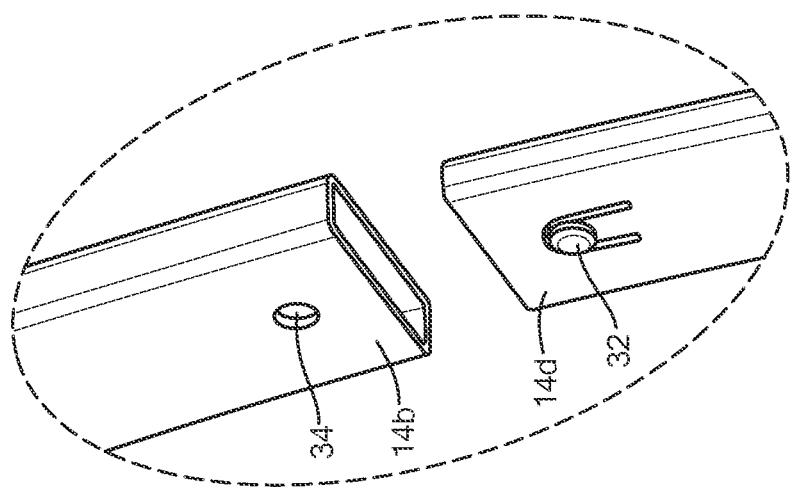
*FIG. 5B*
*FIG. 5A*

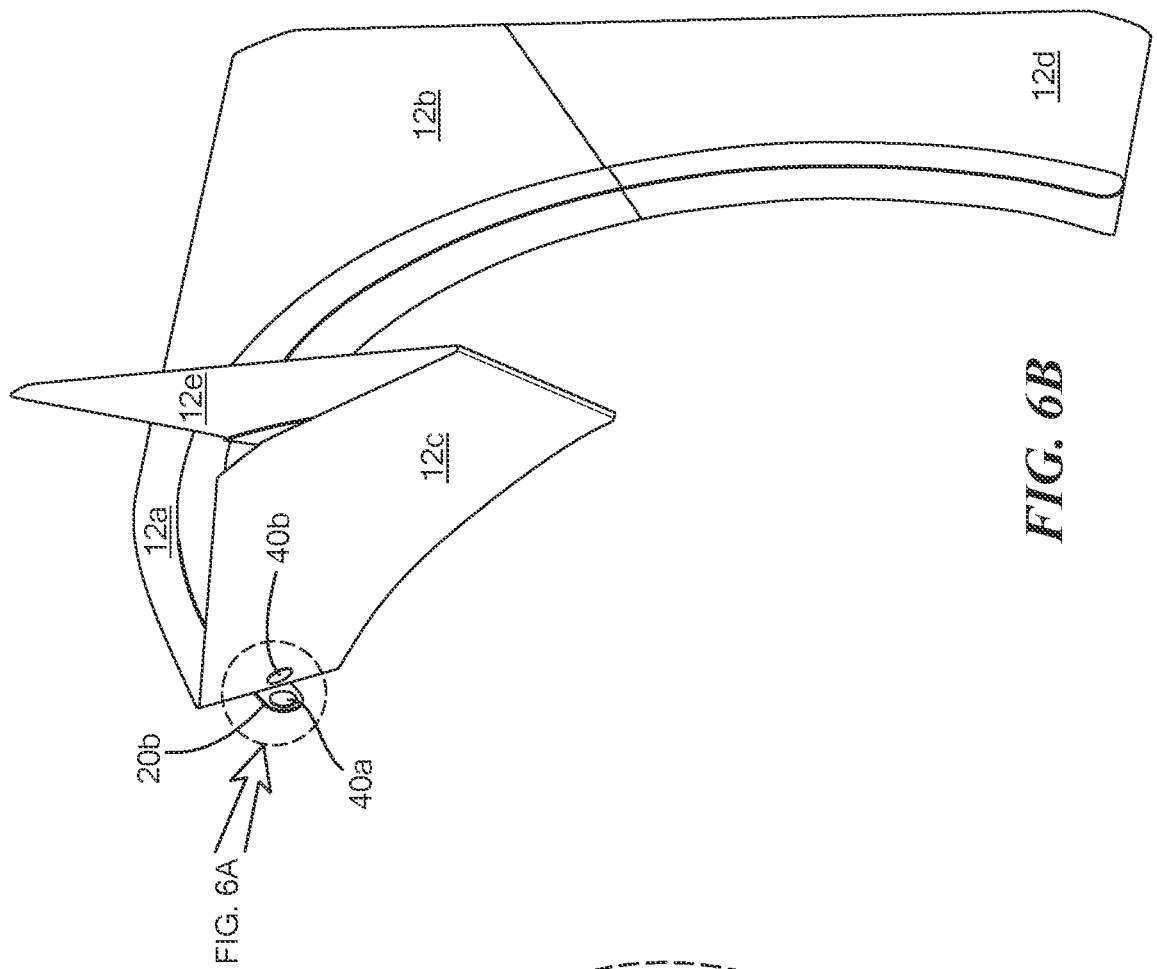
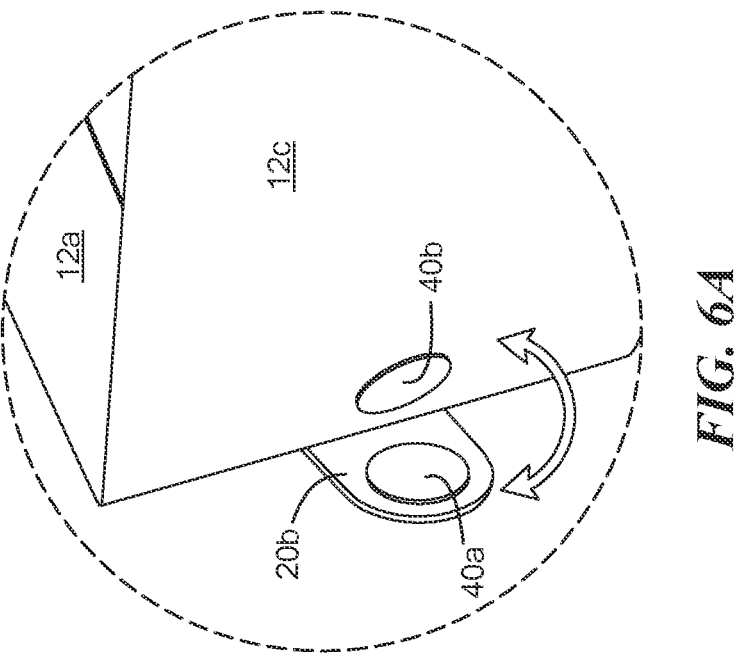
FIG. 6A
FIG. 6B

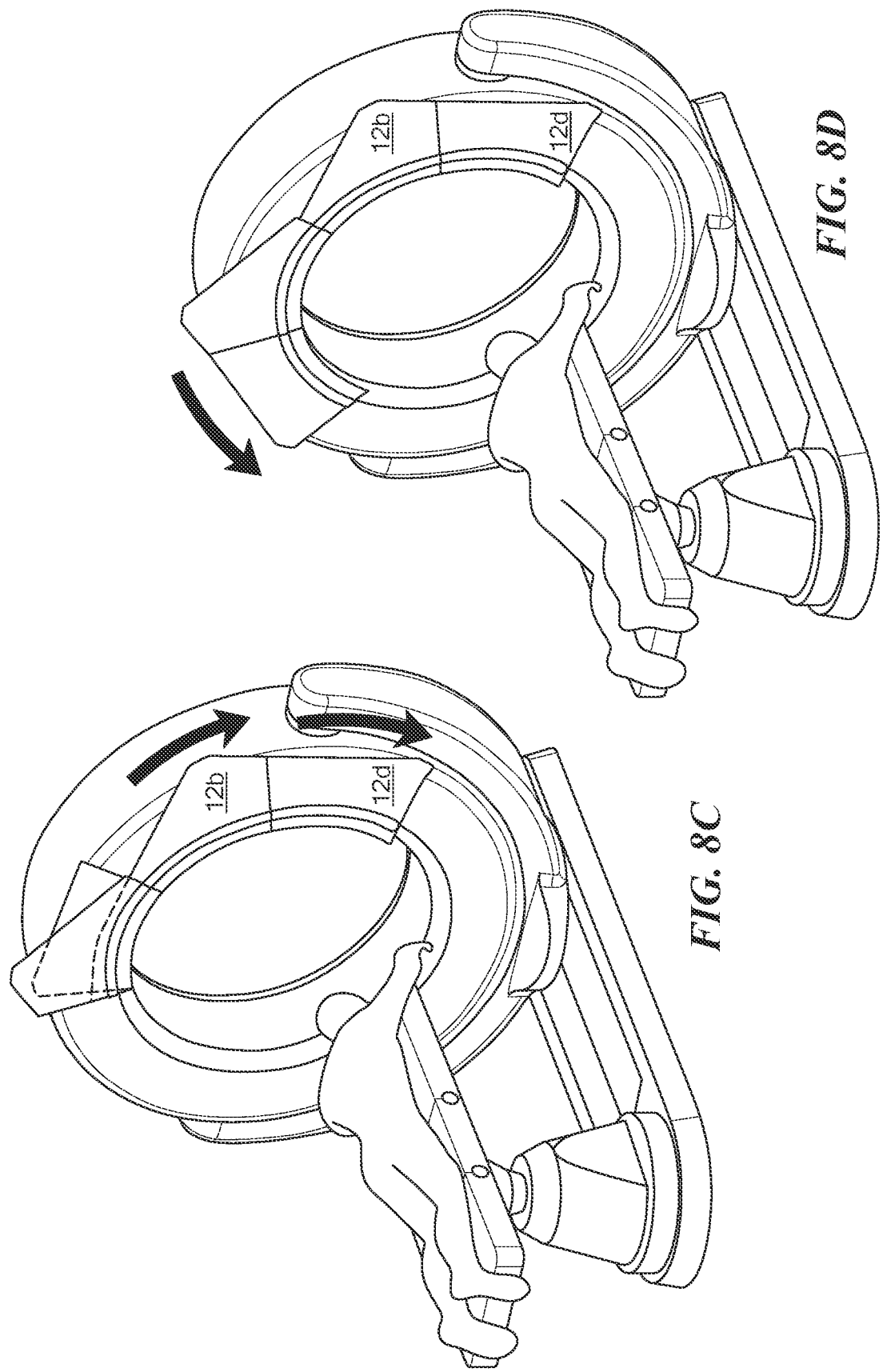

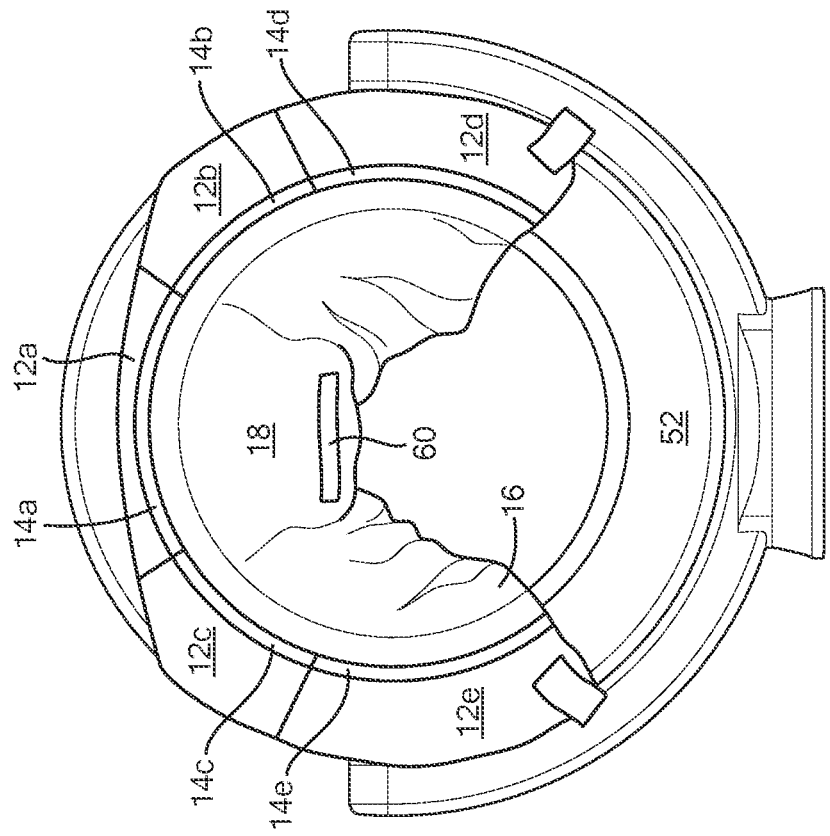
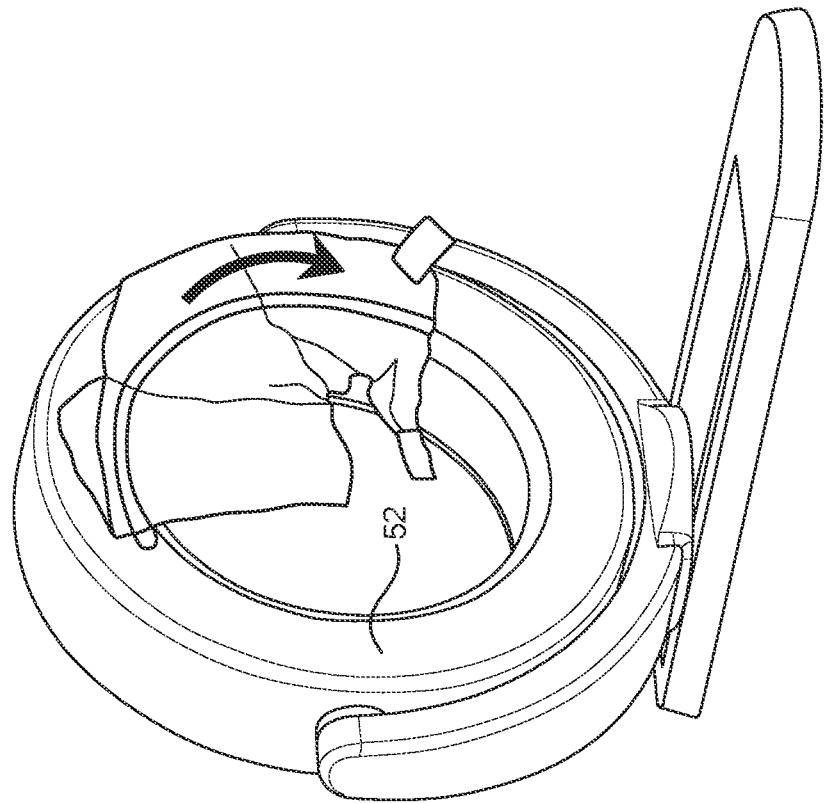
FIG. 9H
FIG. 9G

DRAPE FOR AN IMAGING SYSTEM GANTRY

RELATED APPLICATIONS

This application claims benefit of and priority to U.S. Provisional Application Ser. No. 63/173,689 filed Apr. 12, 2021, under 35 U.S.C. §§ 119, 120, 363, 365, and 37 C.F.R. § 1.55 and § 1.78, which is incorporated herein by this reference.

FIELD OF THE INVENTION

This subject invention relates to drapes protecting the gantry of an imaging system such as a computerized tomography (CT) machine to establish a sterile barrier to protect the patient and to drape to create a protective barrier for other uses and applications (e.g., a masks used in painting operations).

BACKGROUND OF THE INVENTION

Imaging systems such as computerized tomography (CT) machines are often used during surgery. A typical CT machine (e.g., the Mobius Imaging, LLC "Airo" product) includes a gantry with a patient channel therethrough mounted to a gimbal itself mounted to a base. The gimbal can be moved linearly relative to the base. The base also includes a column supporting a patient table which can be moved linearly with respect to the column in and out of the gantry patient channel. See, for example, U.S. Pat. No. 8,770,839 incorporated herein by this reference.

Sterility, of course, is extremely important in the operating theater. If a physician or nurse even touches a non-sterile surface or item, the health care professional must then leave the operating room, rescrub, and don new operating room attire. The CT gantry is considered non-sterile. Breaking sterility can result in increased time and cost associated with surgery.

Accordingly, sterile drapes for imaging machines have been developed. For example, U.S. Published Patent Application No. 2011/0281064 (incorporated herein by this reference) discloses a drape for the patient channel of an imaging machine. The drape is in a form of a sleeve with elastic bands about each opening which are stretched over lips at the patient channel openings of the machine. See also WO2018/0171720 incorporated herein by this reference. See also US. Publication Nos. US2020/0054409 A1 and US2020/0054299-A1.

BRIEF SUMMARY OF THE INVENTION

Still, in some cases, no lips are provided on the gantry. And, it can be difficult and time consuming to deploy drapes without breaking sterility. In many instances, it was so difficult to apply a drape to the gantry that hospital staff "double draped" a patient instead. This is done by having a secondary sterile drape flaked back and ready for each scan. Just prior to the scan, the second drape is unfolded over the patient, clipped carefully so as not to come in contact with the gantry patient channel, and the scan is then taken. The drape is clipped to control it as it moves through the channel. But it has the disadvantage of making direct contact with the non-sterile surface of the gantry as it passes through. So this drape needs to be handled/flaked back very carefully because it will indeed be contaminated. Then, after the scan, the secondary drape is carefully flaked back out of the way to be ready for the next scan.

Featured is a new imaging system gantry patient channel drape which is fast and easy to deploy, fast and easy to remove, and which can be manufactured inexpensively.

The conventional place to open drapes in the OR is on a flat surface (sterile table). So, the new drape concept has been designed to be deployed on a table. Or, it can be deployed directly on the machine. Once deployed, the new drape becomes a (semi) rigid planar object that can safely and controllably be transported to the gantry to be installed. One very practical and long-standing problem with draping any large device in a sterile environment is that these draping options tend to be very large, complicated, and hard to manage. Due to their size, these drapes can be floppy and prone to moving unpredictably due to air currents while being transported and installed. This can lead to contamination that the user may or may not notice. So even if a conventional drape can be fully deployed conventionally (on a sterile table), most drapes large enough to do the job would likely be way too big to manage practically.

Also, a user may want to install the drape after the patient is hooked up to anesthesia tubes that run through the patient channel. In this pre-case scenario, an unsterile patient and anesthesia are oriented with the anesthesia tubes running through the channel. This scenario can happen at the beginning of a case to determine if a patient can safely fit within the channel (a collision check) before the sterile field around the operative site has been established with draping. Once draping of the patient occurs, it is much harder to check for collisions. Also, if a sterile drape is in place at the time of this collision check, and there is an accidental collision with an as yet non-sterile patient, then the sterile drape would become contaminated.

Some users may want a drape that can be installed before or after a collision check is made. Also, if for some unforeseen reason the drape needs to be replaced during a procedure, the new drape can easily be installed at any point of the procedure because it has a non-continuous contour that will fit over the patient and hoses if needed.

The sterile field is meant to protect the surgical site of the patient from infection. However, because the patient can move during the procedure (the operating table has a full range of motion) and the equipment like imaging devices can translate to and over the operative site, it is often necessary for the staff to strictly adhere to some general rules (sometimes called aseptic technique) to preserve the sterile field.

During the busy preparation for a surgery, accidental contamination could occur and easily go unnoticed. Then, the contaminated region on the item could be unwittingly raised back up into the sterile region. The effort and concentration to make sure this doesn't occur can frustrate already busy and overworked staff members that would rather be focusing their attention on patient care and not on the equipment. So, the take away is that if a large sterile drape needs to be transported to the imaging device for installation, it should be made easy to carry within the sterile region safe zone by one or two people. The new drape is compact enough to transport easily within the sterile region/safe zone even when partially assembled.

If the user chooses for any reason to transport the semi-assembled drape, it should be compact enough to easily carry within the sterile area (above the waist). Once attached to the imaging device, segments that protrude down into the non-sterile region can be deployed. This can be achieved axially with hinged segments or radially with telescoping segments.

Once the front side (operative side) of the drape is secured, the remaining sterile material that lines the bore and attaches to the opposing face (back side) needs to be managed. The risk is that even a ("scrubbed") sterile staff member's arms are considered unsterile about two inches above the elbow. Any accidental contact would require removing and replacing the drape. It would also require the staff member to "rescrub". This is a time consuming and costly mistake. Even worse, if this accidental contact goes unnoticed it could compromise the sterile field of the patient during surgery. A spreader (a stay that keeps drape material apart) can be added to the central leaf of the back side of the drape in some embodiments of this design. A method to control this material has been devised to significantly reduce the risk of material accidentally falling on or being drawn towards and onto a non-sterile part of a scrubbed staff member.

As a result, securing all sterile drape mounts to the machine from one side is now quite easy. The new drape design (in some embodiments) will allow the sterile staff member to secure all sterile mounting points from one side of the device with more control to avoid the risk of contamination. This is valuable because it saves time and provides reliable mitigation against accidental contamination.

One new drape concept is a method/system for giving the sterile staff member(s) control when deploying, handling, transporting, and installing a large sterile (or non-sterile) equipment drapes especially in an OR environment where risk of contamination is of high concern. One purpose of this drape is to establish a barrier against contamination (sterile field) between large (imaging) equipment and the patient's operative site. It preferably relies on a plurality of configurable segments with integrated (semi) rigid stays, hinges, and locking features to give it a (semi) rigid planar quality once configured. It preferably has a non-continuous inner contour (C-Shape).

During normal use, the drape can be configured from a very compact package to a very large device capable of covering very large imaging (or other) equipment. The new drape's general orientation is in respect to the patient. The front side is the side closest to the patient and where the (scrubbed/sterile) surgical staff typically have most contact. The back side is the side furthest from the patient and where the (scrubbed/sterile) surgical staff typically have least direct contact.

Because the new drape may have a lot of parts that move relative to one another, it is useful to have a means of describing these element's orientation to each other. The new drape uses a clockface orientation to describe the general position of each element. For example, segments will be referred to as "12 o'clock", "2 o'clock," "10 o'clock," etc.

The new drape through its many variants preferably employs several key features. Segments are sections or leaves of the drape that can move (rotate/translate) independently to allow the drape to be configured. In most configurations, these segments will be made of plastic sheeting, but could also be made of semi-rigid material (ex: card stock, card board). Stays are what (in most configurations) give the otherwise flexible segments their structure and allow the drape to be deployed, configured, and installed with a high degree of control. In some cases, stays will be permanently bonded to the segments (hinged concept). In other scenarios, the stays may move freely within channels or pockets within the segments (telescoping concept). In the concepts shown, some stays (12, 2, and 10 o'clock) may have automatic locking features that fix their relative orientation to adjacent segments once they have reached their intended limit of travel. A spreader is an (semi) rigid element meant to improve the handling of loose drape material during installation. The spreader allows the installer to safely pass the sterile drape material through the imaging bore and complete installation on the far side of the machine. Locking features are automatic/passive features that fix (semi) rigid stays to each other once they have reached their intended limit of travel. Some examples of locking mechanisms that could be effectively employed are Velcro, spring loaded snap features, tape, etc. Mounting features preferably are used to secure and mount the new drape to the (imaging) device being draped. These are similar to locking features (above) in that Velcro is often used. However, these elements correspond to defined mounting locations on the equipment. These keep the drape attached to the machine but allow for pulling out slack and getting rid of creases.

The drape packs up small but once deployed, it covers the large and critical areas of the imaging system.

Once deployed, the drape preferably becomes a semi-rigid planar assembly. This semi-rigid quality greatly improves the sterile staff member's ability to control the drape during transport to the imaging device, and during installation. This semi-rigid feature is also what gives these assemblies an "anchor". This rigid quality prevents drape material from being pulled through the bore while being mounted to the opposing side. This feature also allows the drape to be pulled taught which is optimal to avoid creases or catch points.

In one design, the drape has three main sections. When mounted, the drape has a front face (closest to operative site), a truncated cylinder which covers the inner diameter of the scanner, and a back face. The front and back faces can be symmetrical or they can have different contours. The drape can mount to the imaging system with Velcro (or similar). The drape may utilize hand holds (mitts) to prevent accidental contamination. In some iterations sterile helper cards may be utilized for safe transfer between sterile and non-sterile staff. There are embodiments of this design that use only MRI compatible materials, have telescoping sections that attach to and move with parts of the gantry that move, may have closed off areas to accommodate neuro applications and embodiments that are suited for non-sterile applications (aerospace, agriculture, etc.).

The drape design preferably utilizes an open (inner diameter) contour, or "C" shape. Rather than relying on a hoop spring for automatic deployment, variants of the drape concept expand: axially with hinged segments or radially with telescoping segments. Rather than relying on a hoop spring to give it a semi-rigid planar quality, it relies on a plurality of stays that can be configured and in some cases affixed to one another.

The drape has several variants that depend on the clinical application and/or the equipment being draped: with hinged segments that open axially, telescoping segments that open radially, or a combination of both telescoping and hinged segments.

Featured in one example is an imaging system drape comprising a gantry first outer side wall covering portion including a top leaf and one or more adjacent leaves on opposite sides of the top leaf. There is a stay for each leaf. A gantry inner wall covering portion extends from the gantry first outer side wall covering portion and one or more drape portions attached to the gantry inner wall covering portion are securable to a gantry second outer side wall.

In one version, the stays are interconnected. For example, the stays are hinged to each other or the stays telescope relative to each other. The drape may further include a member such as a strap securing the top leaf to an adjacent leaf. In one example, each stay is bonded to its respective leaf.

The drape first outer side wall covering portion, the gantry inner wall covering portion, and the one or more drape portions are preferably made of plastic. In one version, the one or more drape portions form a gantry second outer side wall covering portion. A stay member may be associated with the gantry second outer side wall covering portion. A first fastener can be associated with the gantry second outer side wall covering portion and is mateable with a second fastener on the gantry second outer side wall covering portion.

The drape may further include one or more hand sleeves associated with the gantry second outer side wall covering portion, and/or one or more hand sleeves associated with one or more said leaves of the gantry first outer side wall covering portion.

The drape may further include a first fastener associated with one or more leaves mateable with a second fastener on the gantry first outer side wall. The one or more drape portions may each include retainers securing the drape to the gantry second outer side wall.

The drape may further include a patient envelope portion. In one example, the patient envelope portion extends from the gantry inner wall covering portion outwardly through the gantry. The patient envelope portion may include a patient fenestration located at a terminal portion of the patient envelope portion. The patient envelope portion may include a stiffener forming a patient viewing window.

Also featured is a method of securing a drape to an imaging system gantry. The preferred method comprises securing a gantry first outer side wall covering portion top leaf to a top portion of the gantry first outer side wall. An adjacent leaf is deployed to cover a gantry first outer side wall lower portion on one side of the top portion. Another adjacent leaf is then deployed to cover a gantry first outer side wall lower portion on an opposite side of the top portion.

The method may further include deploying additional leaves to cover additional lower portions of the gantry first outer side wall. The method may further include deploying a gantry inner wall covering portion which extends from the gantry first outer side wall covering portion and attaching one or more drape portions attached to the gantry inner wall covering portion and to a gantry second outer side wall. The method may further include deploying a patient envelope portion which extends from the gantry inner wall covering portion outwardly through the gantry.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 5A-5B show releasably interconnected locked stays;

FIGS. 6A-6B show a strap interconnected between and locking adjacent leaves;

FIGS. 8A-8E show the deployment sequence for a drape with telescoping stay;

DETAILED DESCRIPTION OF THE INVENTION

Figure 1:
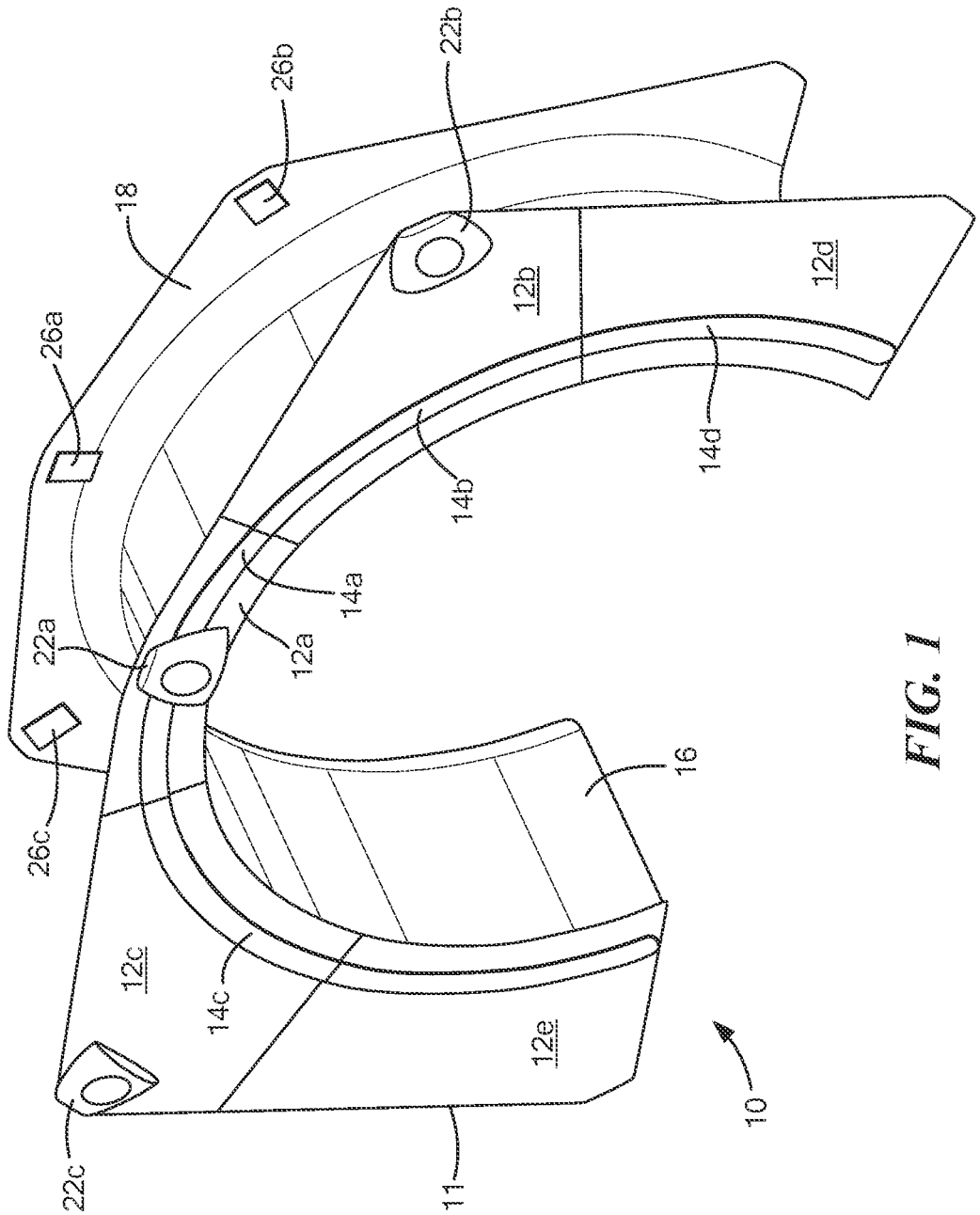
FIGS. 1-2 depict an example of an imaging drape.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
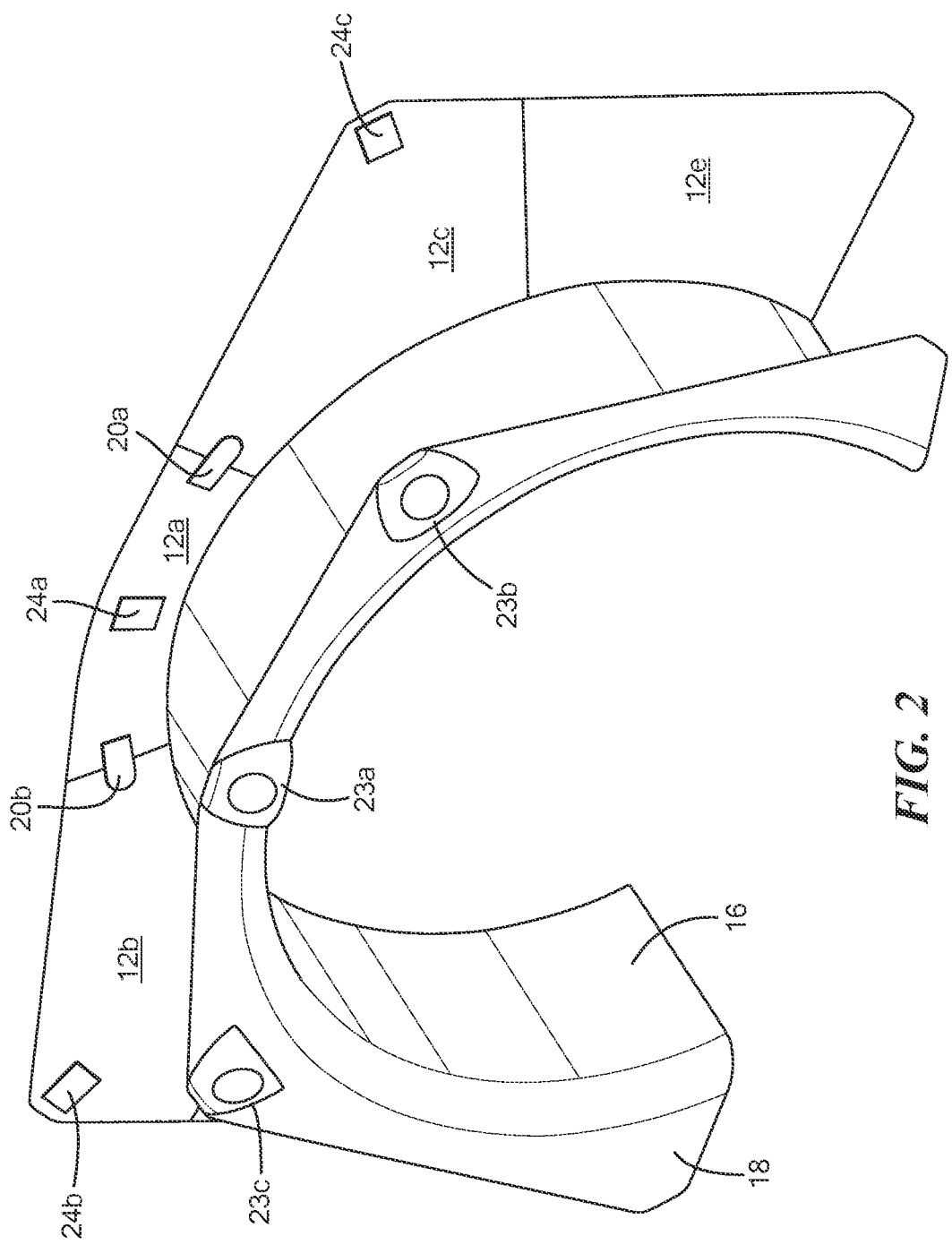
Figure 3A:
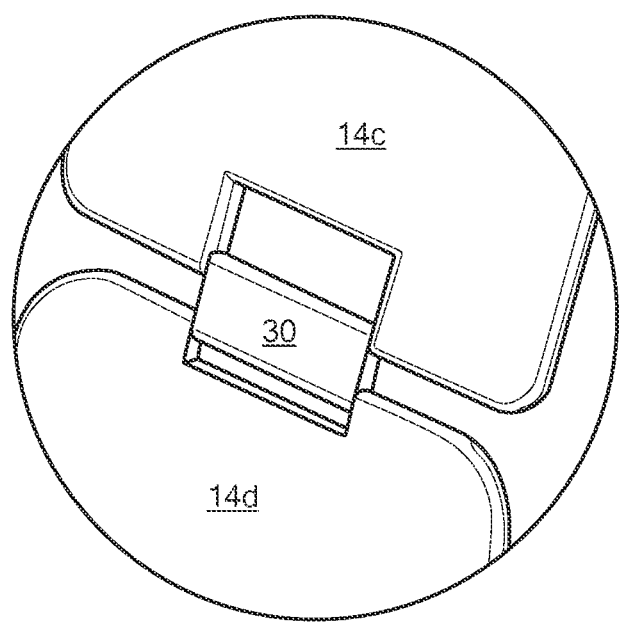
FIGS. 3A-3B show how adjacent stays may be hingedly interconnected.
Figure 3B:
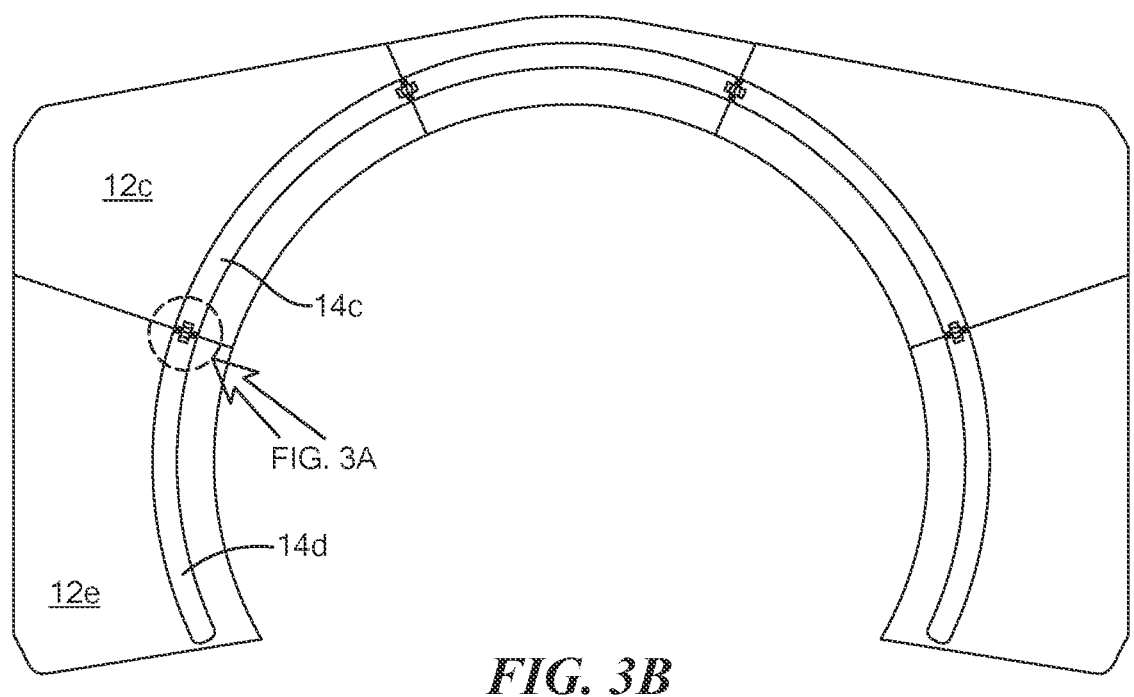

FIGS. 1-2 show an example of an imaging system C-shaped drape 10. Gantry first outer side wall covering portion 11 includes top leaf 12a, adjacent side leaves 12b and 12c on opposite sides of the top leaf 12a, and additional side leaves 12d and 12e adjacent to side leaves 12b and 12c, respectively. There may be a stay 14a-14e for each leaf. The stays may be bonded to the respective leaves. Gantry inner wall covering portion 16 extends from gantry first outer side wall covering portion 11 and one or more drape portions 18 attached to inner wall covering portion 16 are securable to the gantry second outer side wall forming, in this particular example, a gantry second outer side wall covering portion. Straps 20a and 20b secure leaf 12a to leaves 12c and 12b, respectively, typically via Velcro. Leaves 12a, 12b, and 12c each include hand sleeves 22a, 22b, and 22c, respectively. Leaves 12a, 12b, and 12c may further include Velcro patches 24c, 24b, and 24c, respectively, which releasably mate with Velcro portions on the gantry first outer side wall. Similarly, portion 18 may include Velcro patches 26a, 26b, and 26c which releasably mate with Velcro patches on the gantry second outer side wall portion. Portion 18 may also include sleeves, such as sleeves 23a-23c.

Figure 4A:
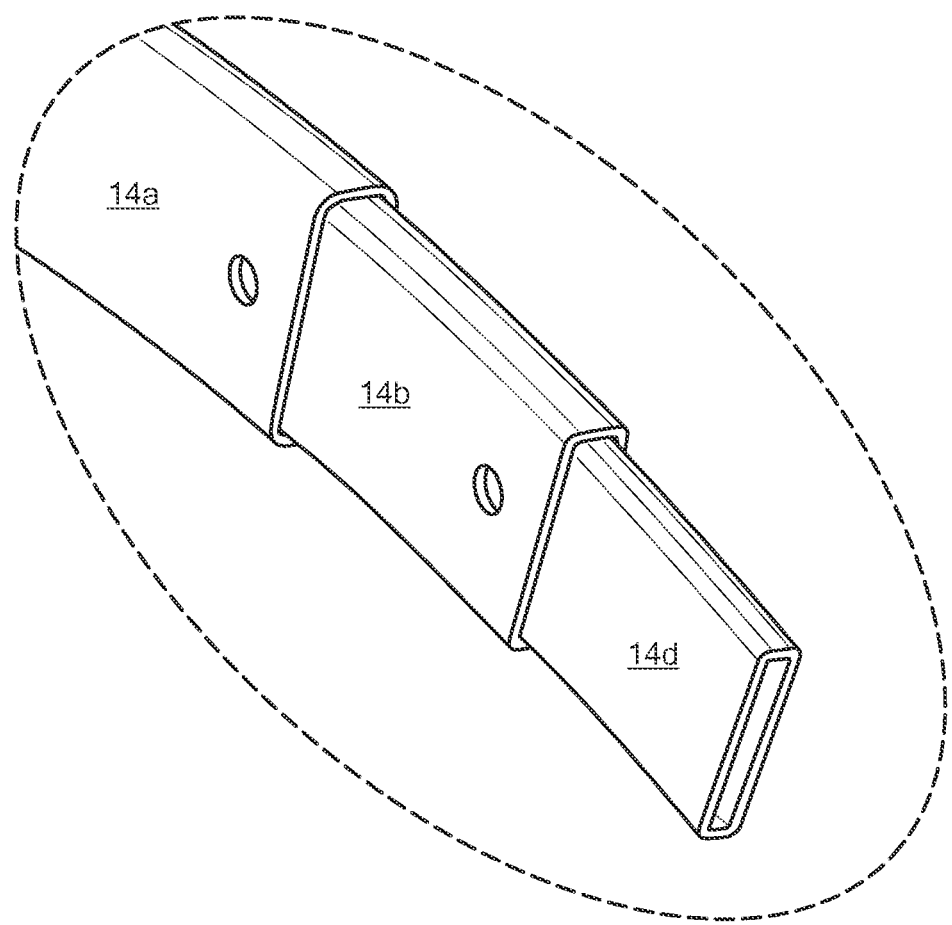
FIGS. 4A-4B show how the stays may telescope relative to each other.
Figure 4B:
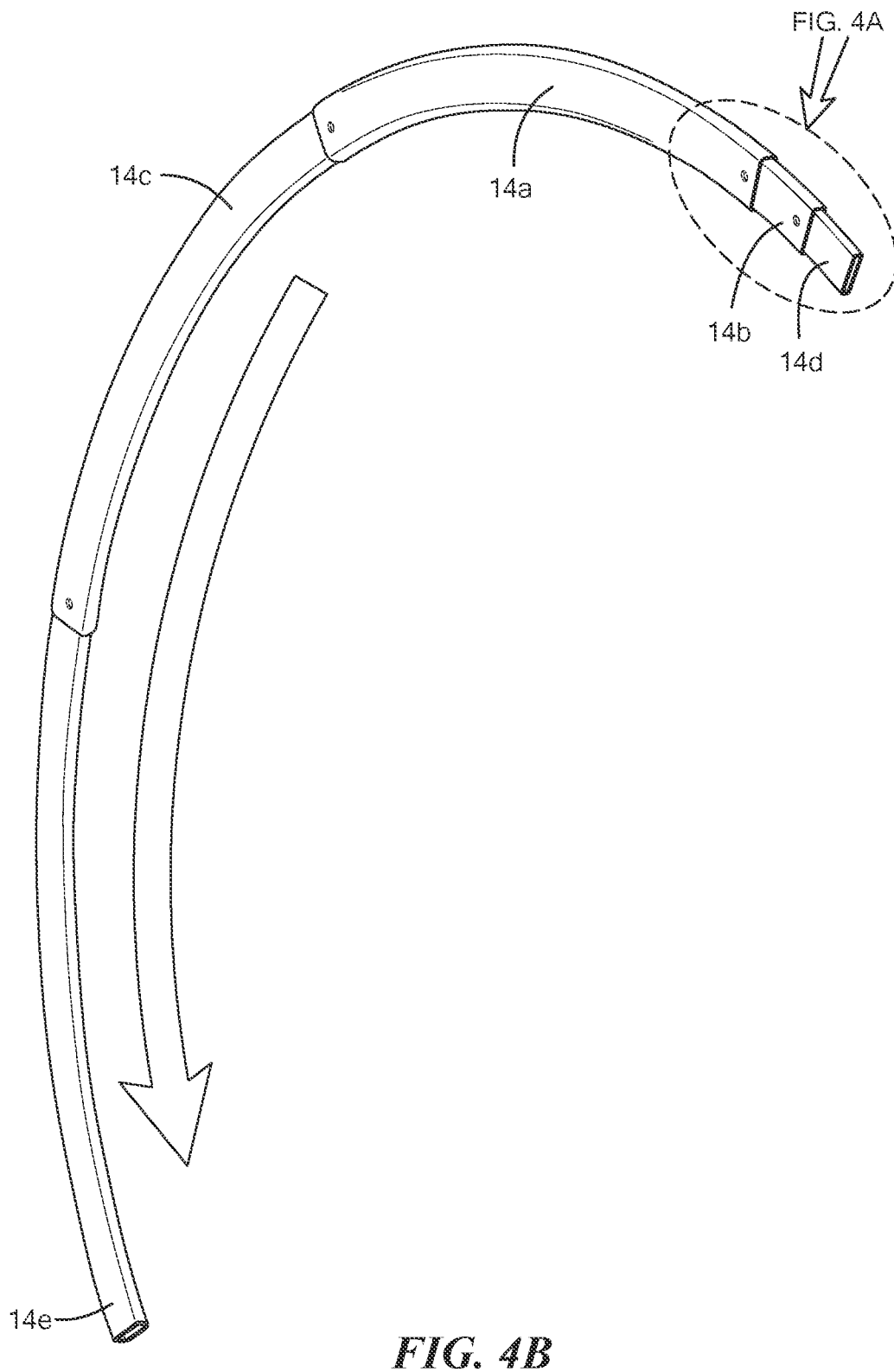

The stays 14 may be interconnected. As shown in FIGS. 3A-38, the distal end of stay 14c may be hingedly attached to the proximal end of stay 14d via hinge member 30. Or, the stays may telescope relative to each other as shown in FIGS. 4A-4B where stay 14d slides within stay 14b which itself slides within stay 14a. In one design, when fully extended, a spring male lock post 32 in the proximal end of stay 14*b* will releasably lock with respect to female lock hole 34 in the distal end of stay 14*b*. The stays could also be disconnected and the drape material between two stays acts as a "hinge".

FIGS. 6A-6B depict how the strap 20*b* attached to leaf 12*a* locks leaf 12*a* to leaf 12*c* when the leaves are deployed. Strap 20*b* includes Velcro patch 40*a* releasably mateable with Velcro patch 40*b* on segment 12*c*.

Figure 7B:
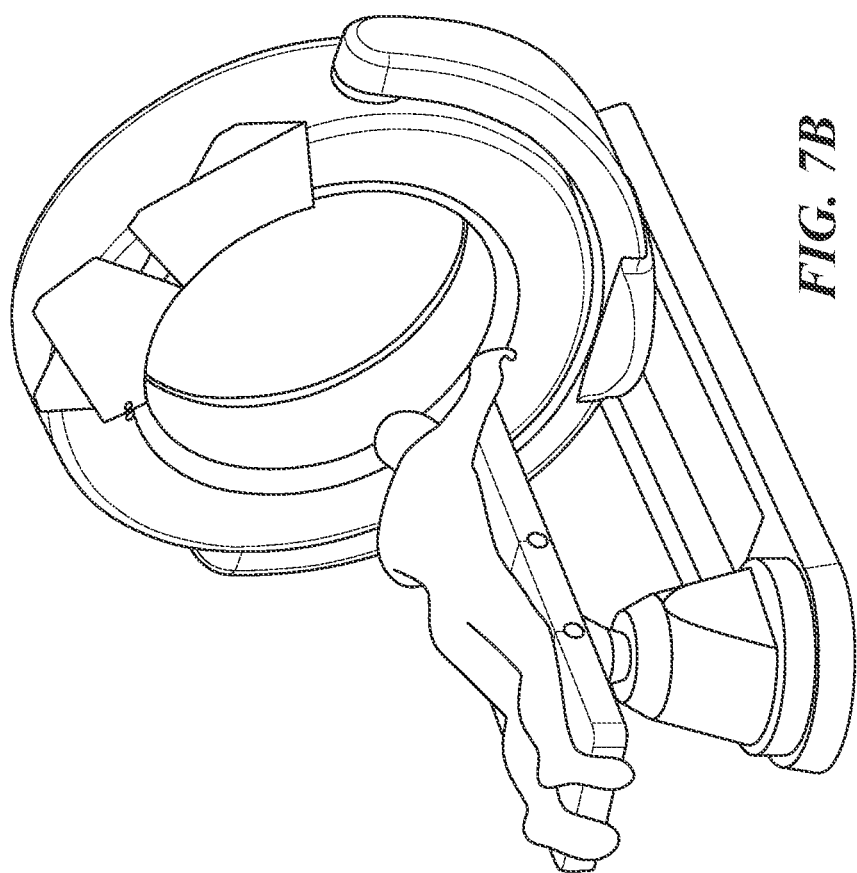
FIGS. 7A-7E show the deployment sequence for a drape with hinged stays.
Figure 7A:
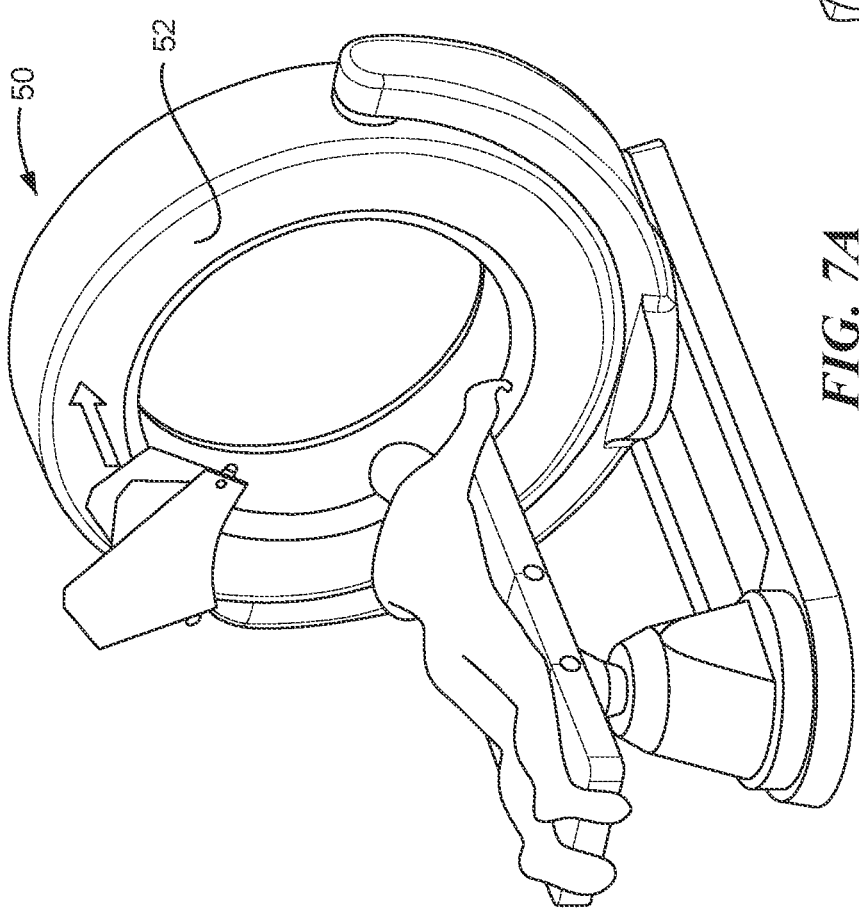
Figure 7D:
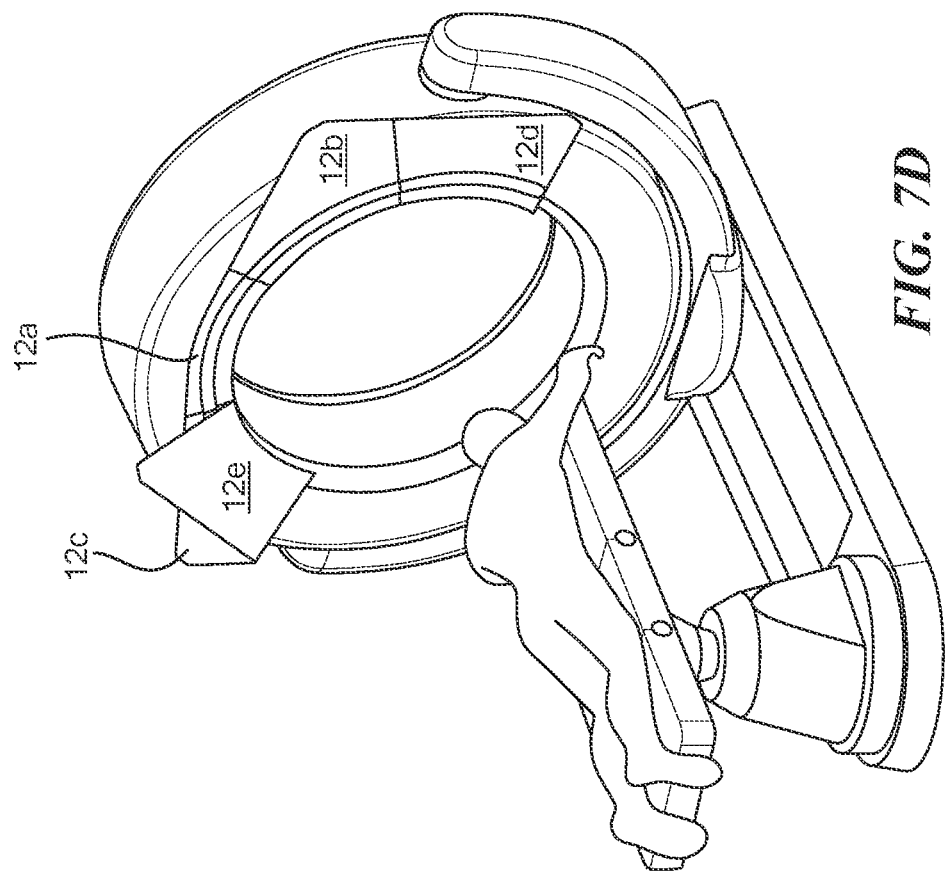
Figure 7C:
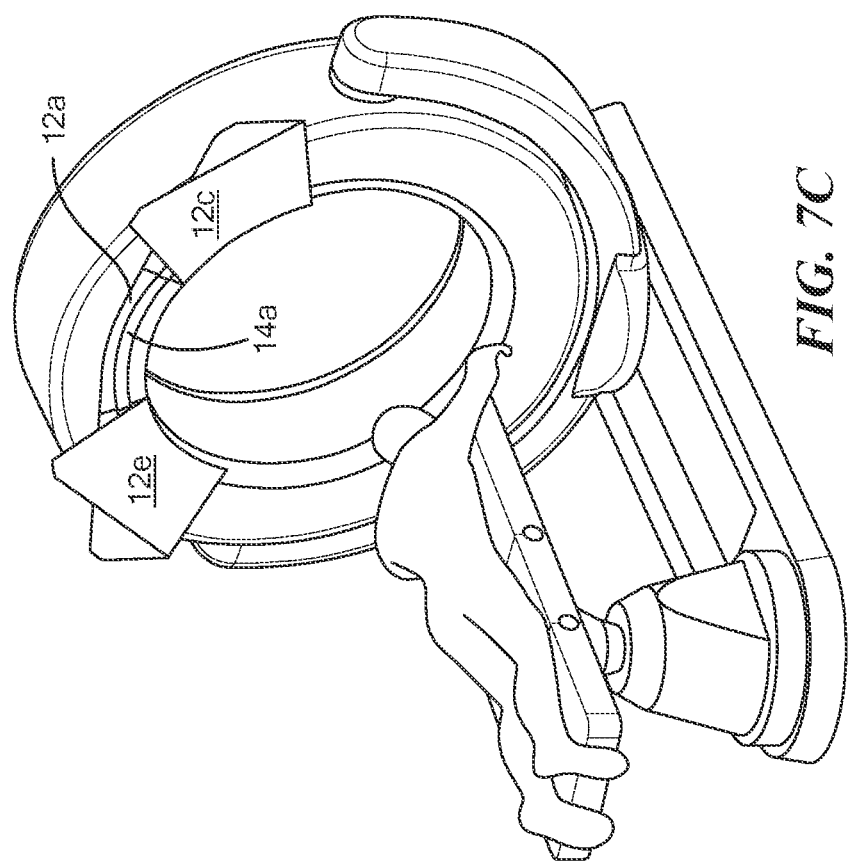

FIGS. 7A-7E depict how a drape with hinged stays is deployed onto an imaging system gantry 50. The top leaf 12*a* is secured to gantry outer side wall 52. FIG. 7A, leaves 14*b* and 14*c* are then deployed. FIGS. 7B-7C, and then leaves 14*d* and 14*e* are deployed, FIGS. 7D-7E. Preferably, the folded drape is secured via Velcro to Velcro patches on the imaging device, the individual leaves are temporarily fixed to each other with Velcro so they will not unfold on their own. In one design, after the 12: o'clock leaf is secured to the gantry the 2 o'clock leaf is rotated and aligns and becomes coplanar with the central/top leaf 12 o'clock leaf and these two leaves are releasably affixed to each other. Next the 10 o'clock leaf is rotated and aligns with and becomes coplanar with the central/top leaf (12 o'clock) and the 10 o'clock leaf and the 12 o'clock leaf are fixed to each other when the 10 o'clock leaf is affixed to the gantry. Next, the lower two leaves are rotated downward. These leaves can be allowed to fall gently via gravity to avoid causing turbulence.

Figure 7E:
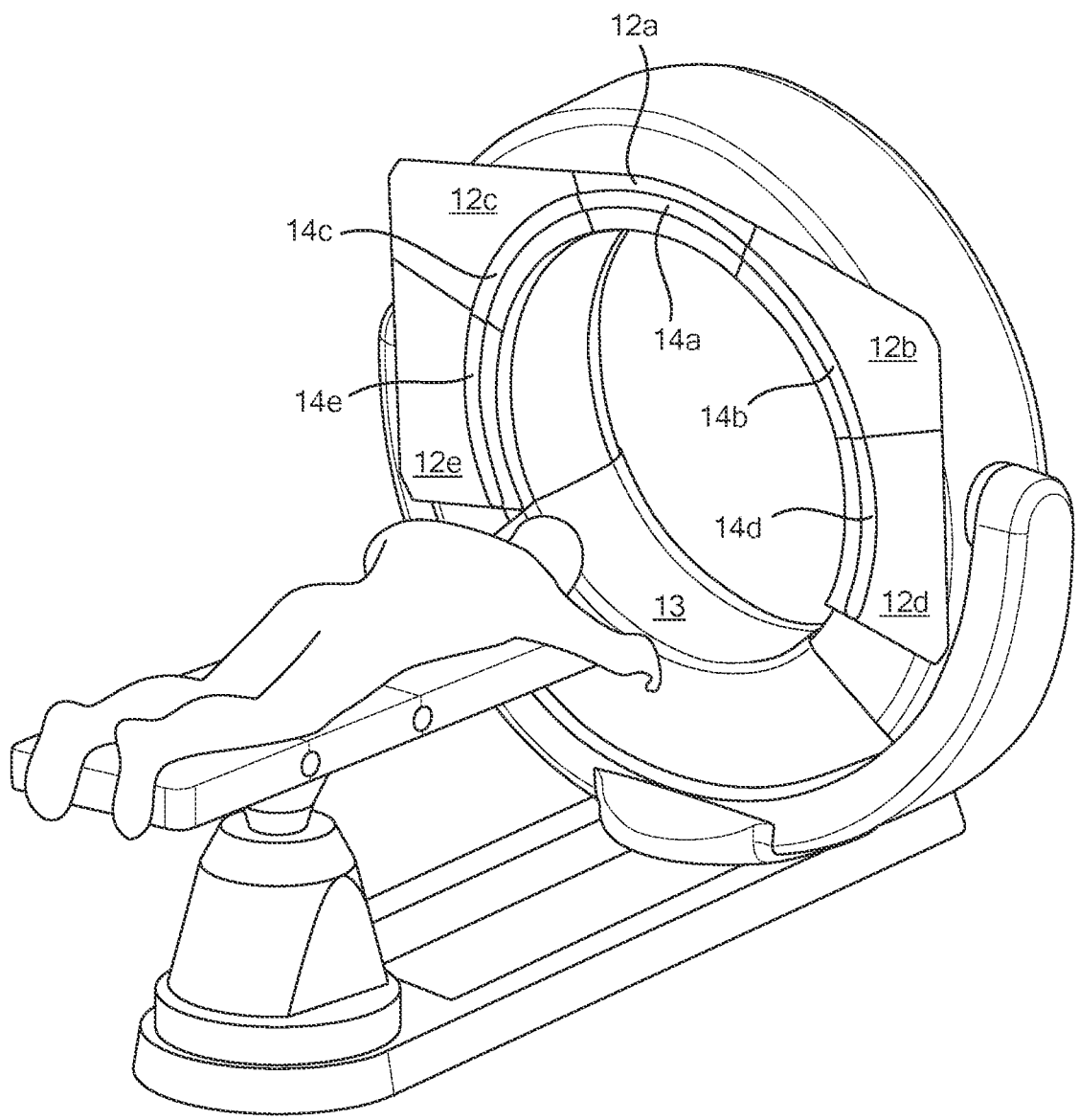

FIG. 7E also shows an optional drape 13 for the lower portion of the CT bore. Its primary purpose is to protect the CT equipment and to reduce clean up time. This bore skirt could be preformed in the shape of the lower CT bore, could include leaves, stays, and the like. Multiple such bore skirts could be used. One example of its use is to prevent blood or other bodily patient fluids from contaminating the CT equipment.

Figures 8A, 8B:
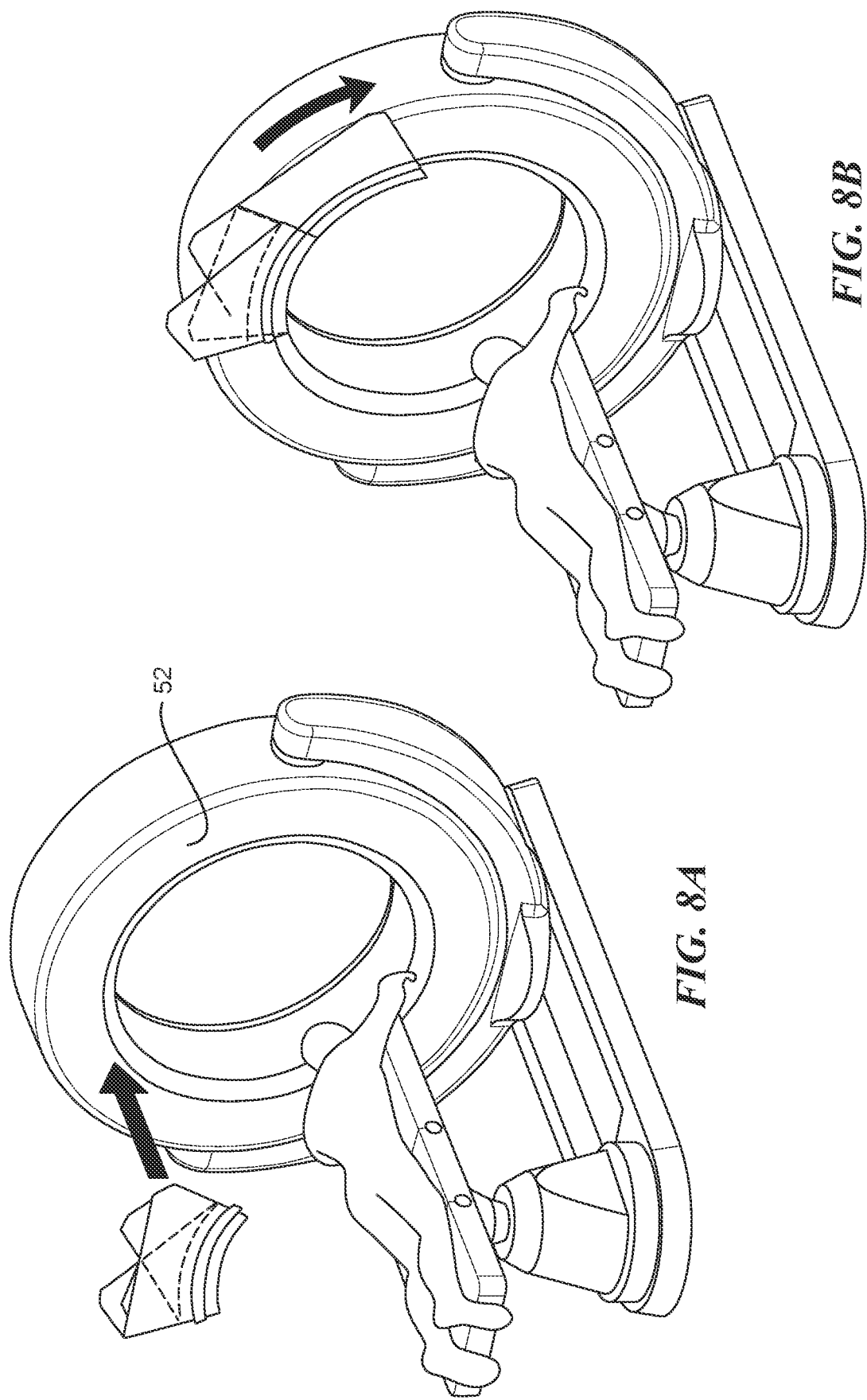
Figure 8E:
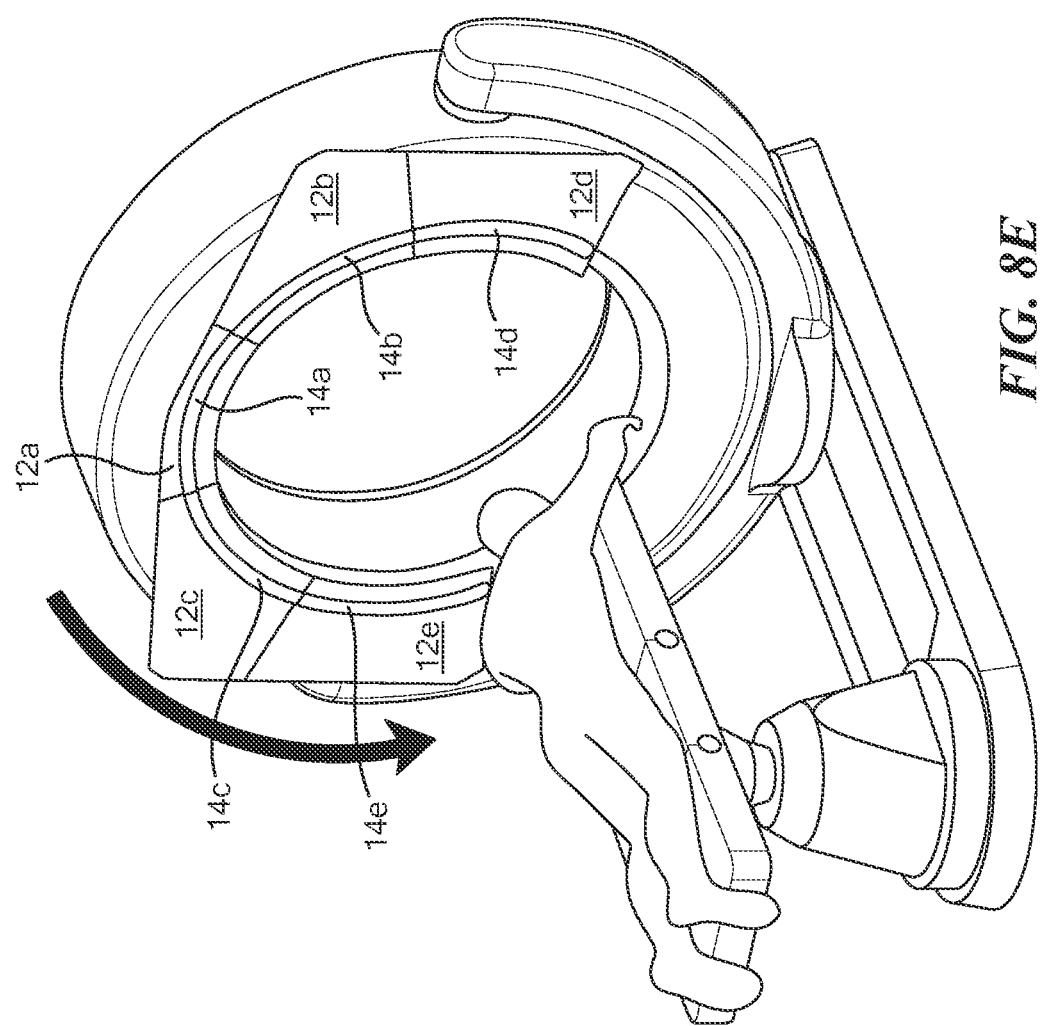

FIGS. 8A-8E depict how a drape with telescoping stays is deployed onto an imaging system gantry. Top leaf 12*a* is secured to the gantry outer side wall 52. FIG. 8A, leaf 12*b* is deployed, FIG. 8B, leaf 12*d* is deployed, FIG. 8C, leaf 12*c* is deployed, FIG. 8D, and then leaf 12*e* is deployed. In one design, the unfolded drape is first secured to respective mounting points on the imaging device. The individual leaves are temporarily affixed to each other with Velcro so they will not unfold on their own. Then, the lower most segment on the right-hand side is rotated and telescoped away from the center segment until it reaches it limit of travel. Once this limit is reached, an inner lock will automatically engage that will affix the position of this segment relative to the closest adjoining segment to prevent the first segment from independently rotating back toward the center segment. Then the second upper right segment is rotated on the right is rotated away from the center segment until it reaches its limit of travel. Once this limit is reached, an inner lock will automatically engage that will affix this segment's position relative to the closest adjoining segment (the center segment) and prevent the second segment from independently rotating back towards the center segment. This segment is then secured to the machine by aligning and affixing a Velcro mounting point on the drape to the corresponding mounting point of the scanner. Then, the first (lowest most) segment on the left side is rotated and telescoped away from the center segment until it reaches it limit of travel. Once its limit is reached, an inner lock would automatically engage that will affix this segment's position relative to the closest adjoining segment and prevent this first segment from independently rotating back towards the center segment. Finally, this second (upper right) segment on the left is rotated/telescoped away from the center segment until it reaches its limit of travel. Again, once this limit is reached, the inner lock will automatically engage and affix this segment relative to the center segment.

Figure 9B:
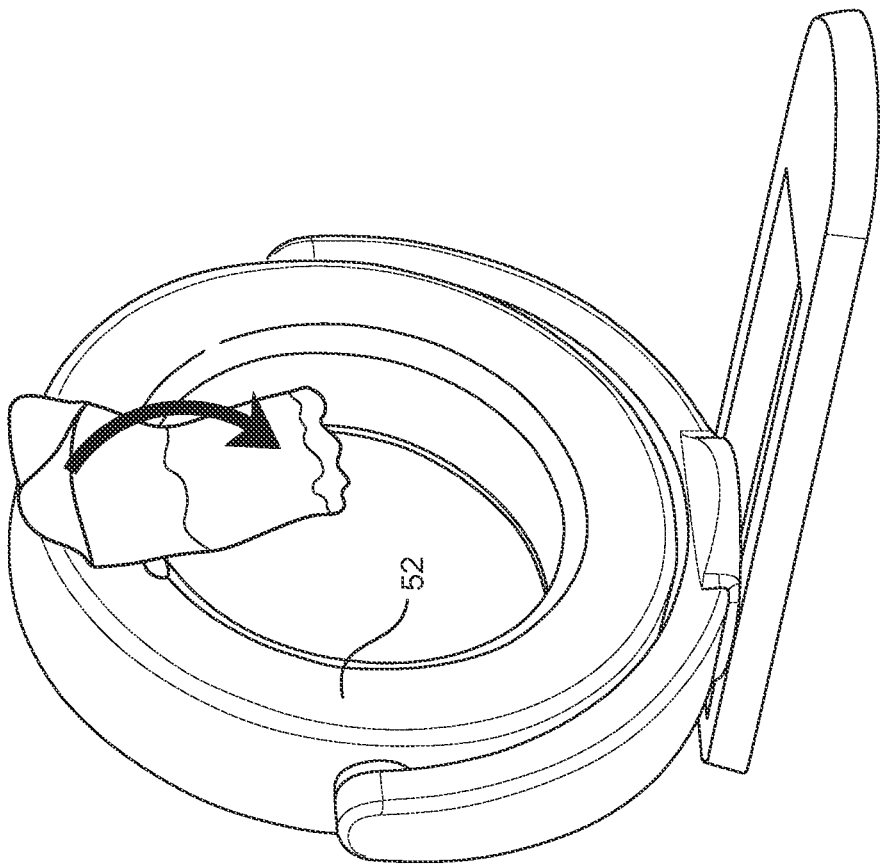
FIGS. 9A-9J again show the deployment sequence for a complete drape.
Figure 9A:
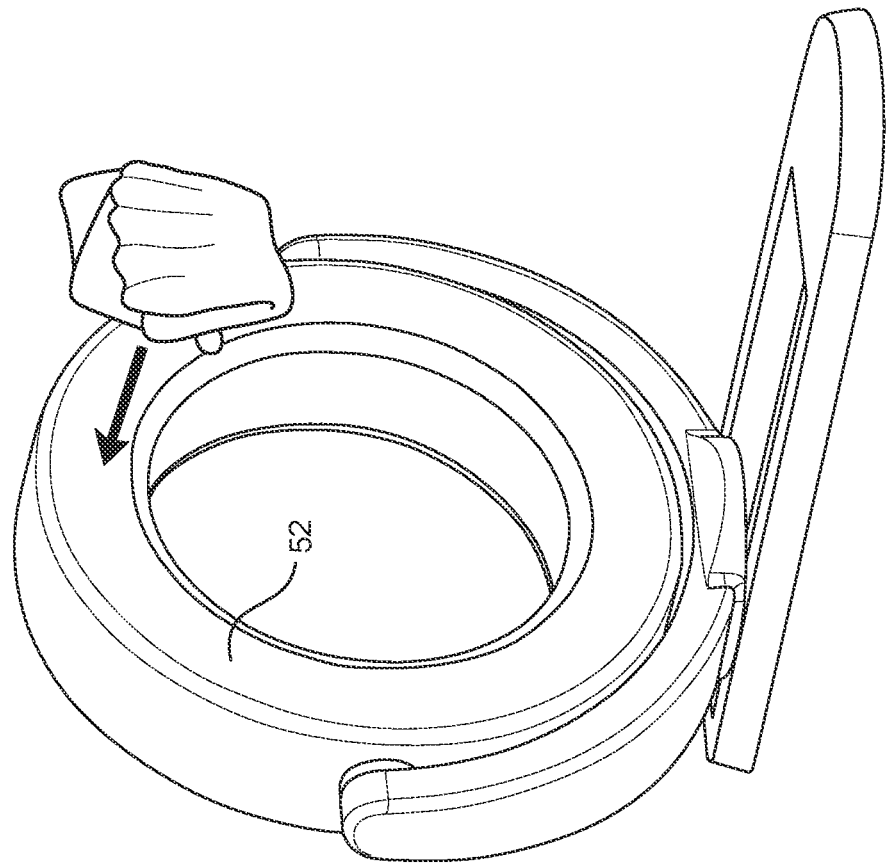
Figure 9D:
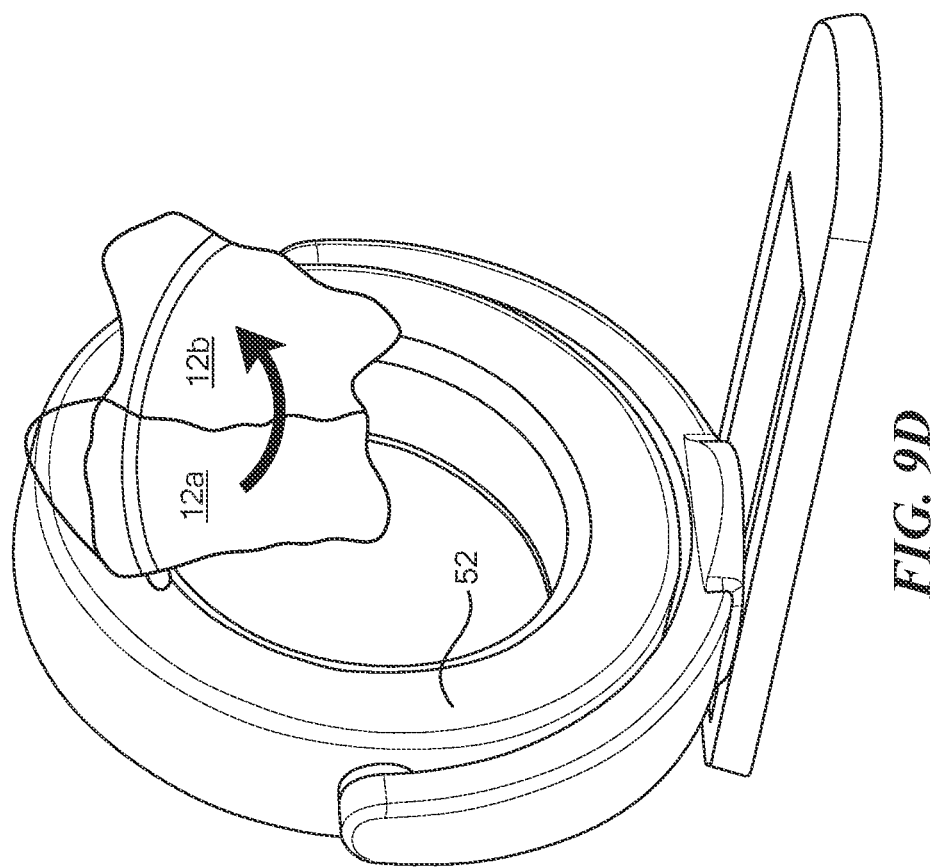
Figure 9C:
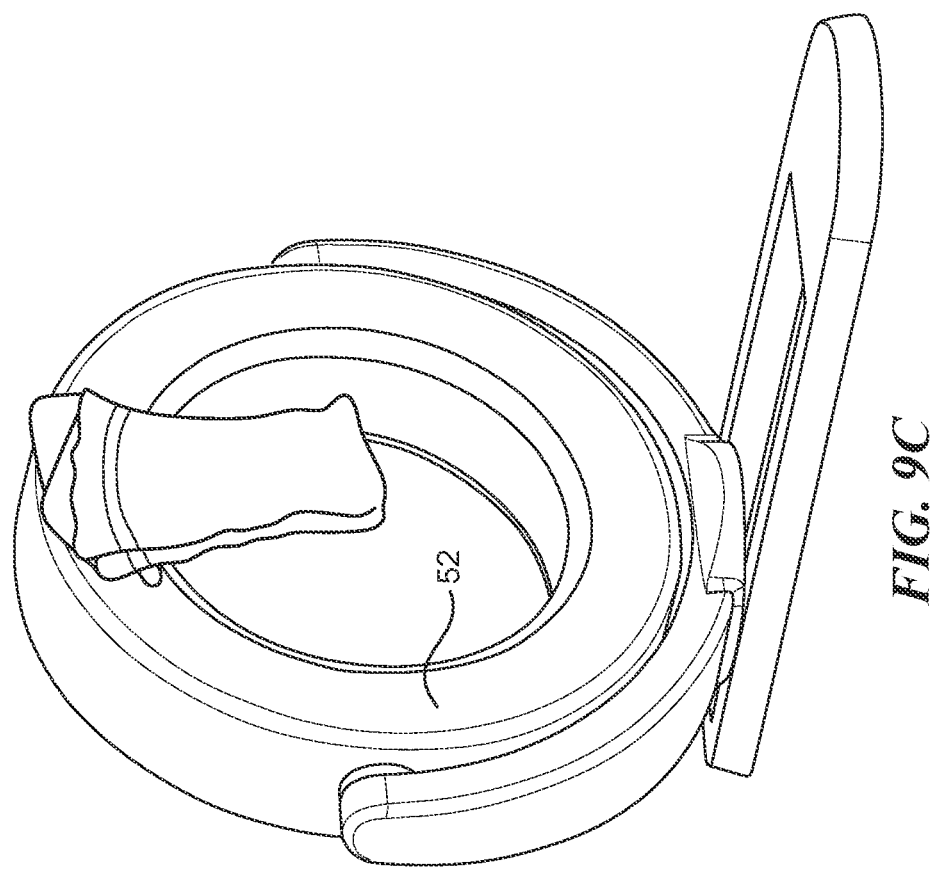
Figure 9F:
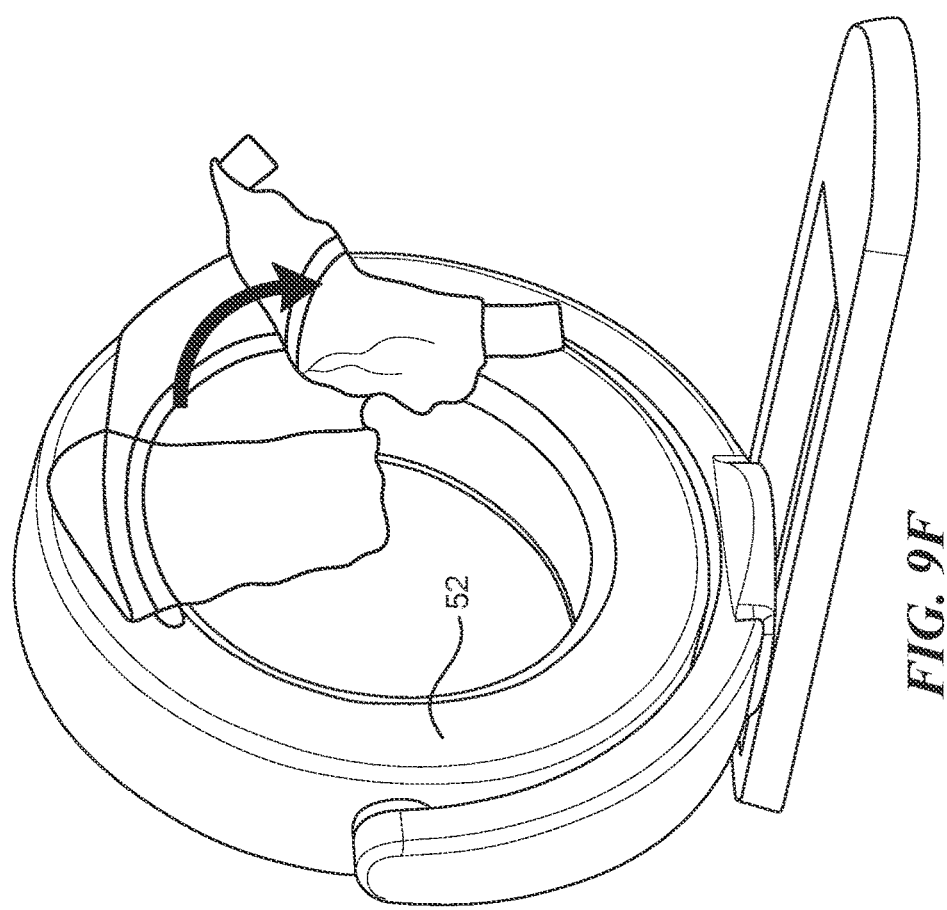
Figure 9E:
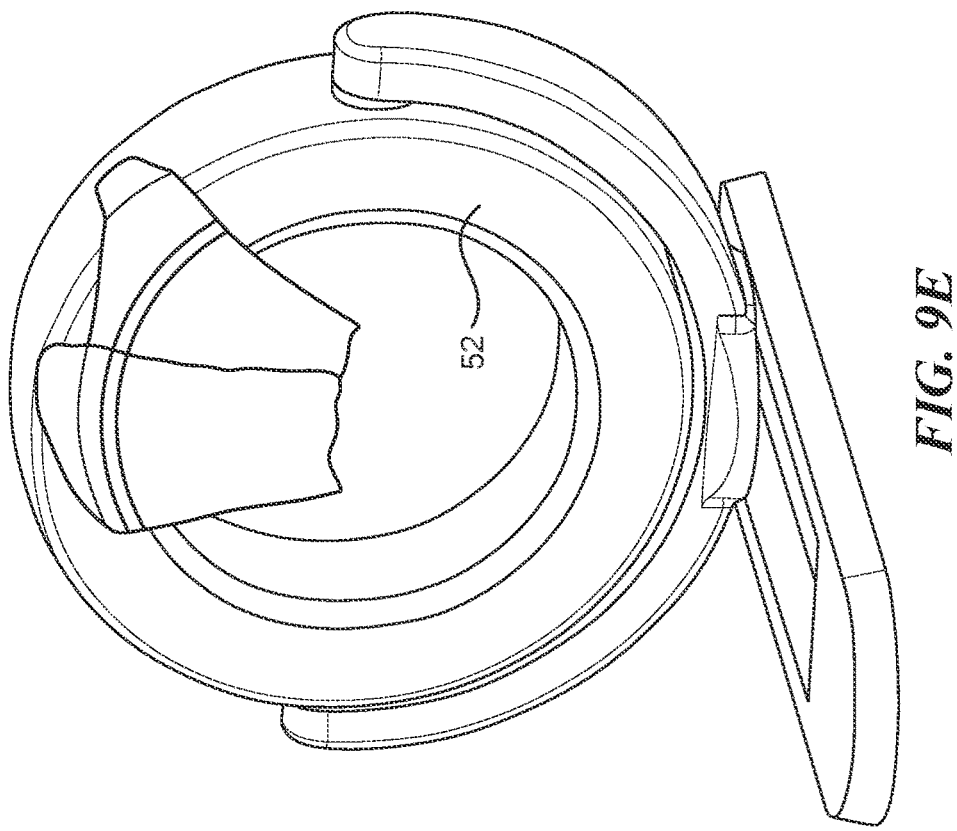
Figure 9I:
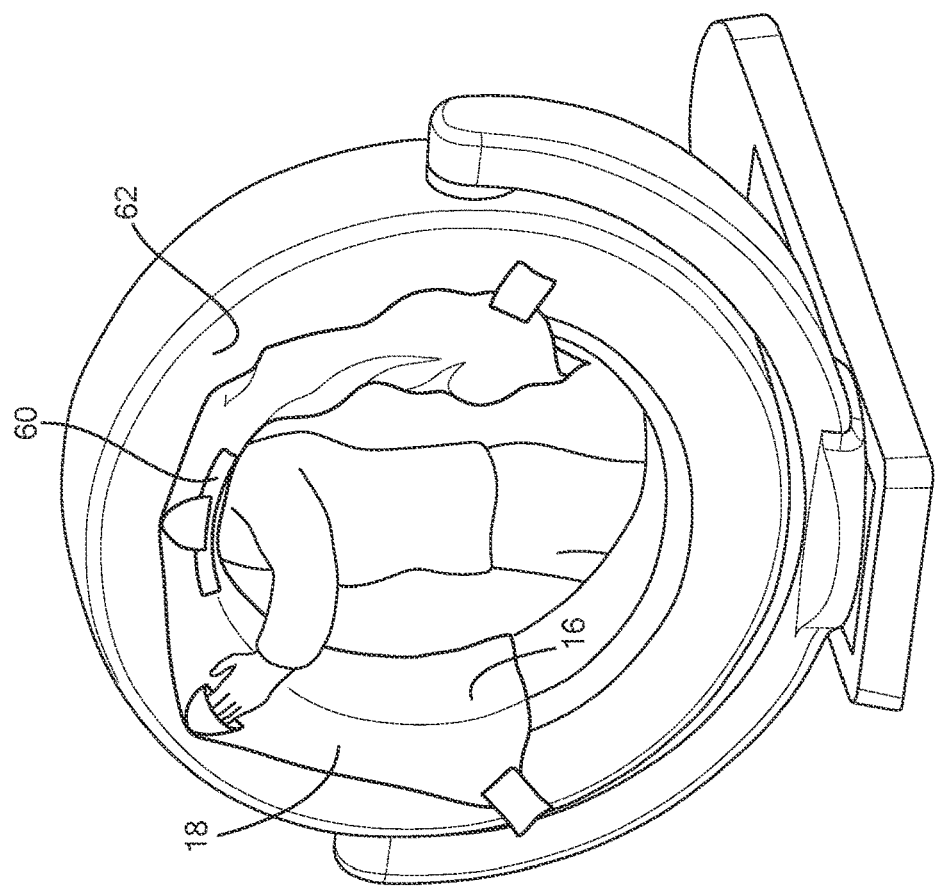
Figure 9J:
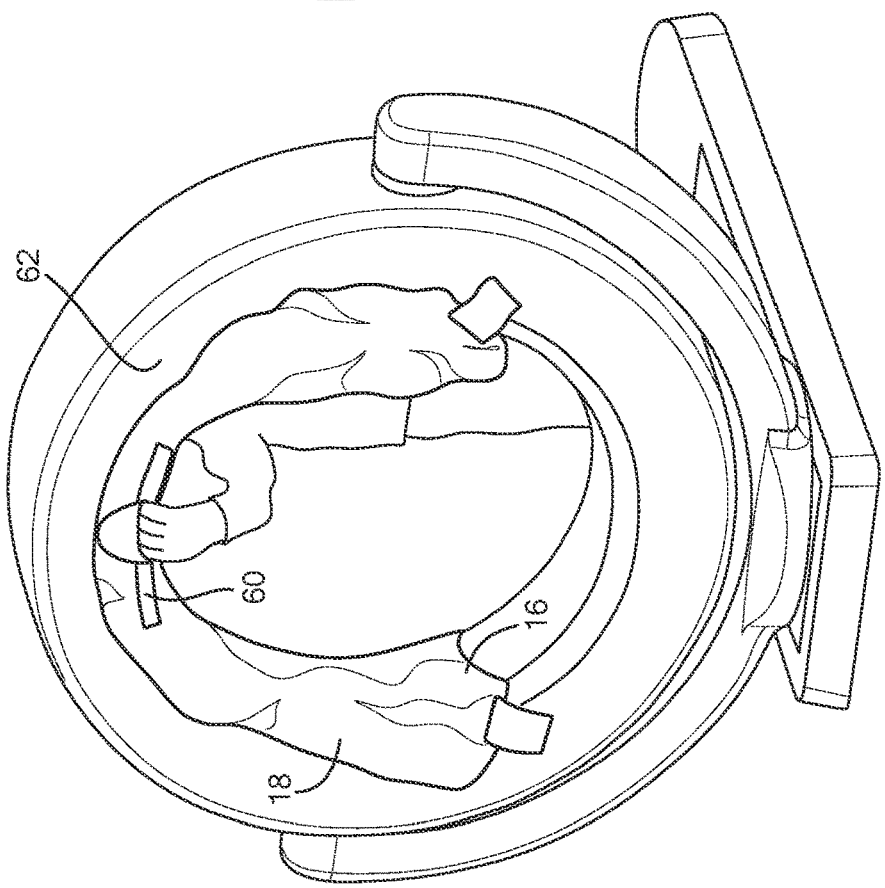
Figure 9K:
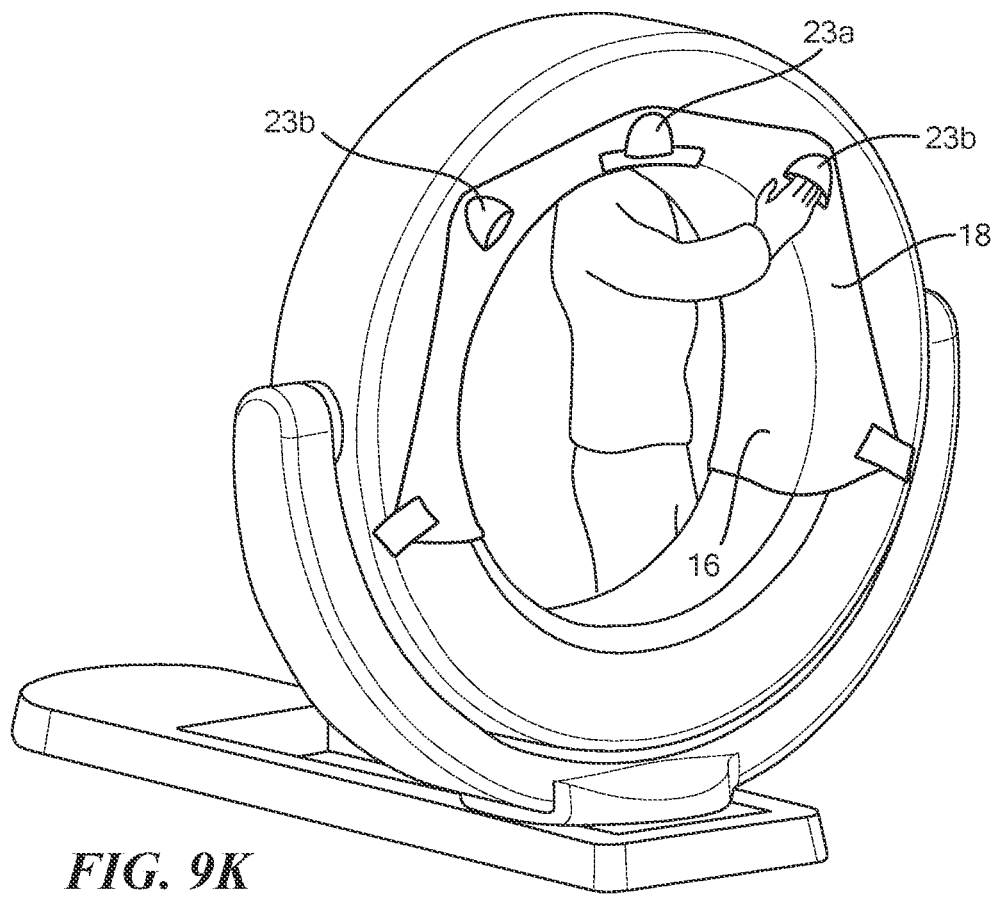
Figure 9L:
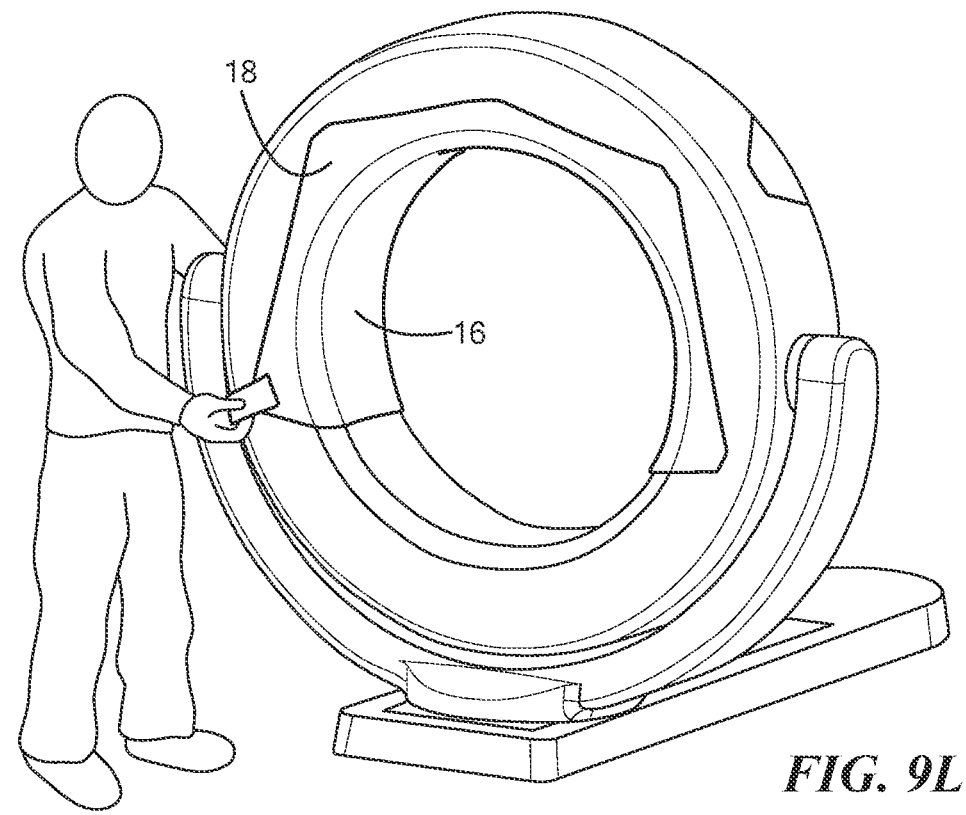

FIGS. 9A-9J show how the complete drape is deployed with the assistance of a stay 60 associated with gantry second outer side wall 62 covering portion 18. Leaf 12*a* is secured to gantry outer side wall 52. FIG. 9A and the remainder of the drape is unfolded, FIGS. 9B-9C. FIG. 9A shows attaching the folded drape to Velcro mounting points on the imaging system; FIG. 9B show unfolding the drape by rotating material downward towards the center of the imaging bore; FIG. 9C shows unfolding the drape; FIG. 9D shows rotating the 2 o'clock segment outward away from folded bundle so that it lies flat and becomes locked to its neighbor the 12 o'clock segment; FIG. 9E shows using the integrated sterile hand hold, securing the 2 o'clock segments upper mounting point to the imaging system; FIG. 9F shows unfolding and rotating the 4 o'clock segment downward and away from it neighbor the 2 o'clock segment; FIG. 9G shows that it is important to not reach below the sterile field (your waist) on this step, so it is okay to let the 4 o'clock segment fall with gravity. In FIG. 9H steps 3 and 4 are repeated on the left side of the drape. First rotate the 10 o'clock segment away from the center so it is aligned (coplanar) and becomes locked to the 12 o'clock segment. Then allow the 4 o'clock segment to drop. FIG. 9H shows using the spreader to keep errant material from accidentally making contact, reach through the imaging system's bore and attach the upper most and central segment (the back side 12 o'clock position) to the corresponding mounting point on the machine. FIG. 9J shows reaching through the bore attach the back side's 10 o'clock segment to its corresponding mounting point on the machine. FIG. 9K shows reaching through the bore attach the back side's 2 o'clock segment to its corresponding mounting point on the machine. FIG. 9L shows how a non-sterile staff member can now pull the drape taunt and secure the remaining four lower mounting points by using the non-sterile helper card. One the card has been used it can be torn away and discarded.

Figure 10:
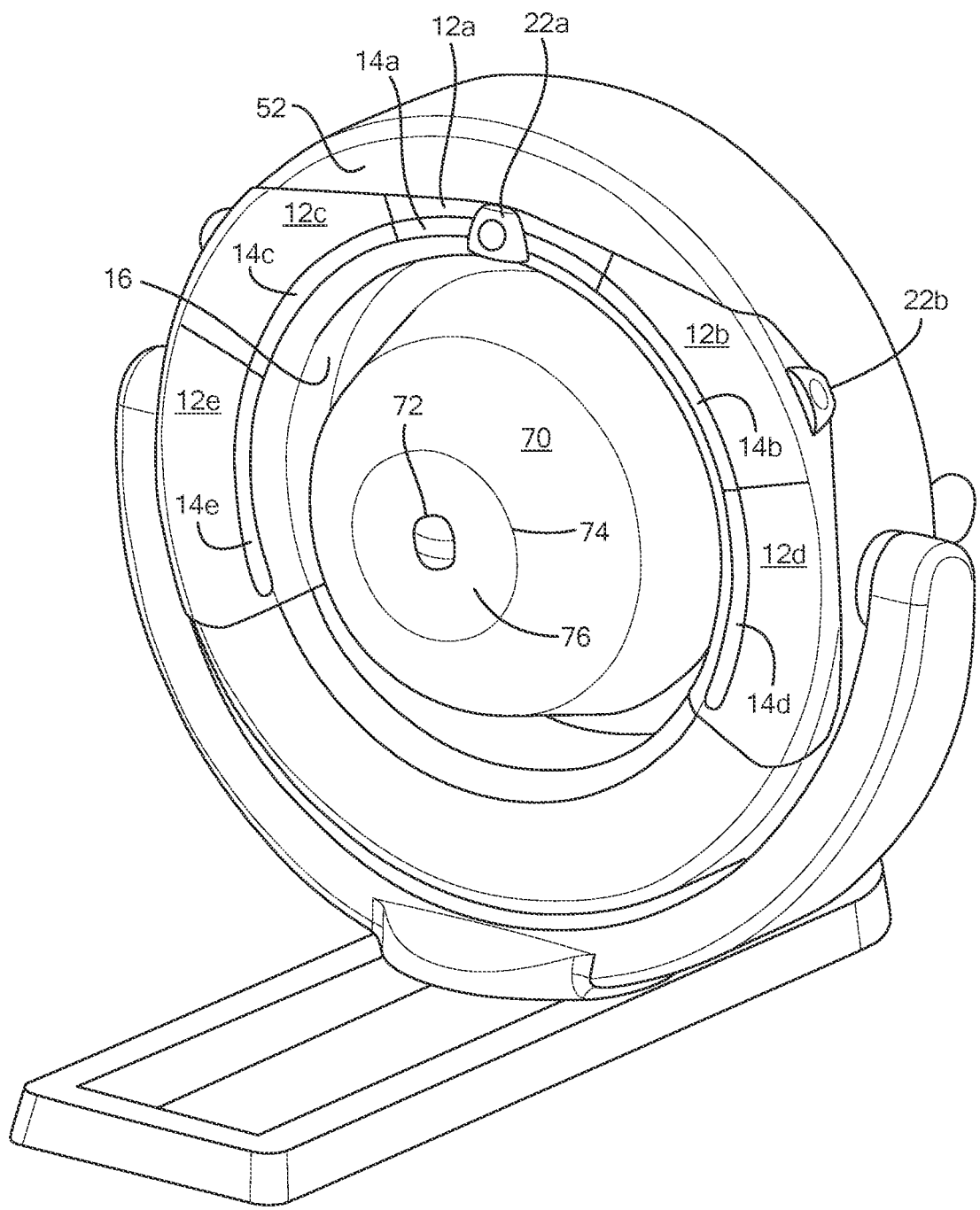
FIGS. 10-11 show an example of a drape with a patient envelope portion.
Figure 11:
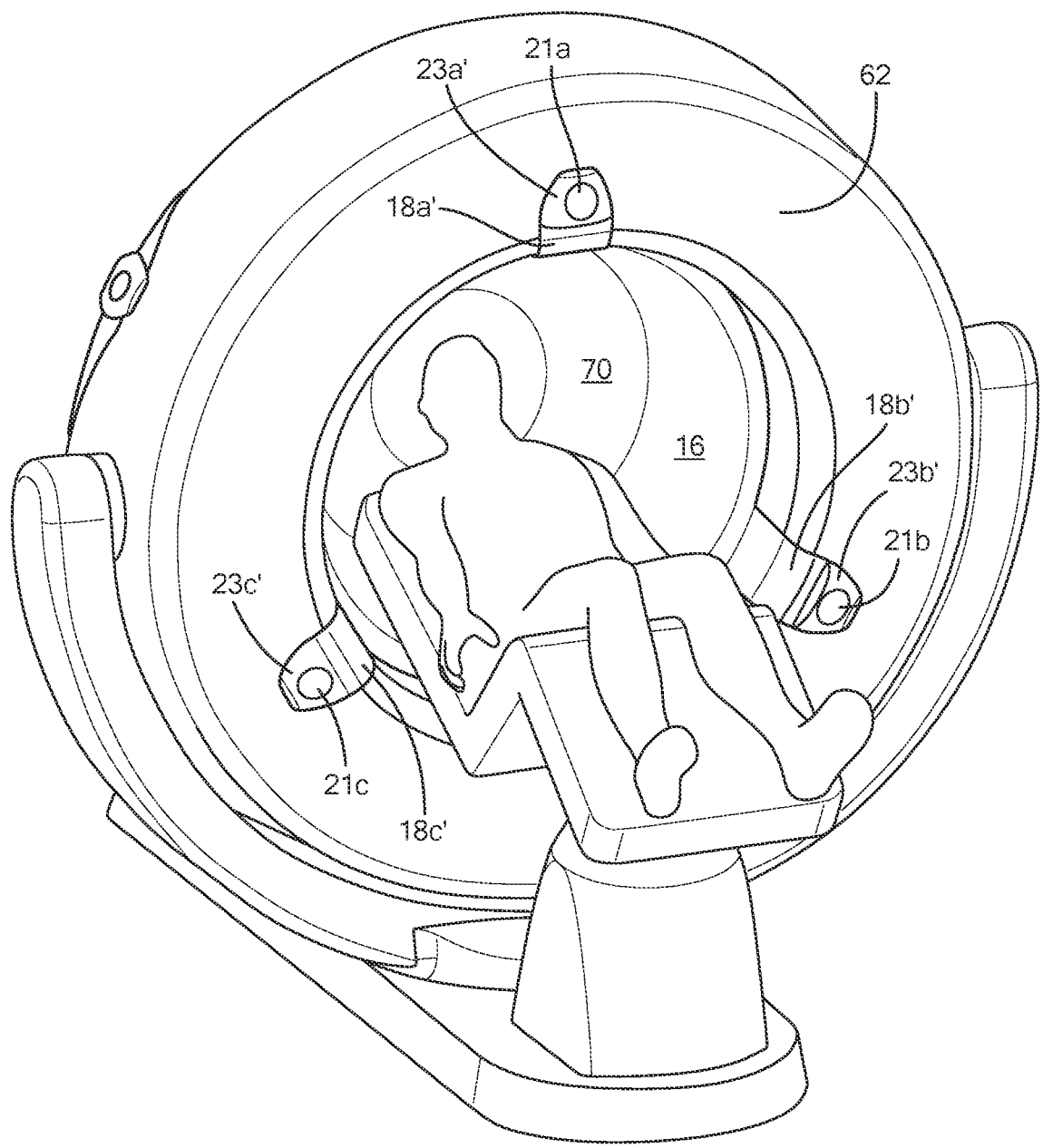

FIGS. 10-11 depict an example of a drape with patient envelope portion 70 extending from gantry inner wall covering portion 16 outwardly through the gantry. Envelope portion 70 may include patient fenestration 72 at a terminal portion of the envelope. Stiffener 74 may be used to define patient window 76. Here, portions 18*a*', 18*b*', and 18*c*' are attached to inner gantry wall covering portion 16 and are secured to gantry second outer side wall 62 via Velcro patches 21*a*-21*c* on sleeves 23*a*', 23*b*', and 23*c*', respectively.

Figure 12A:
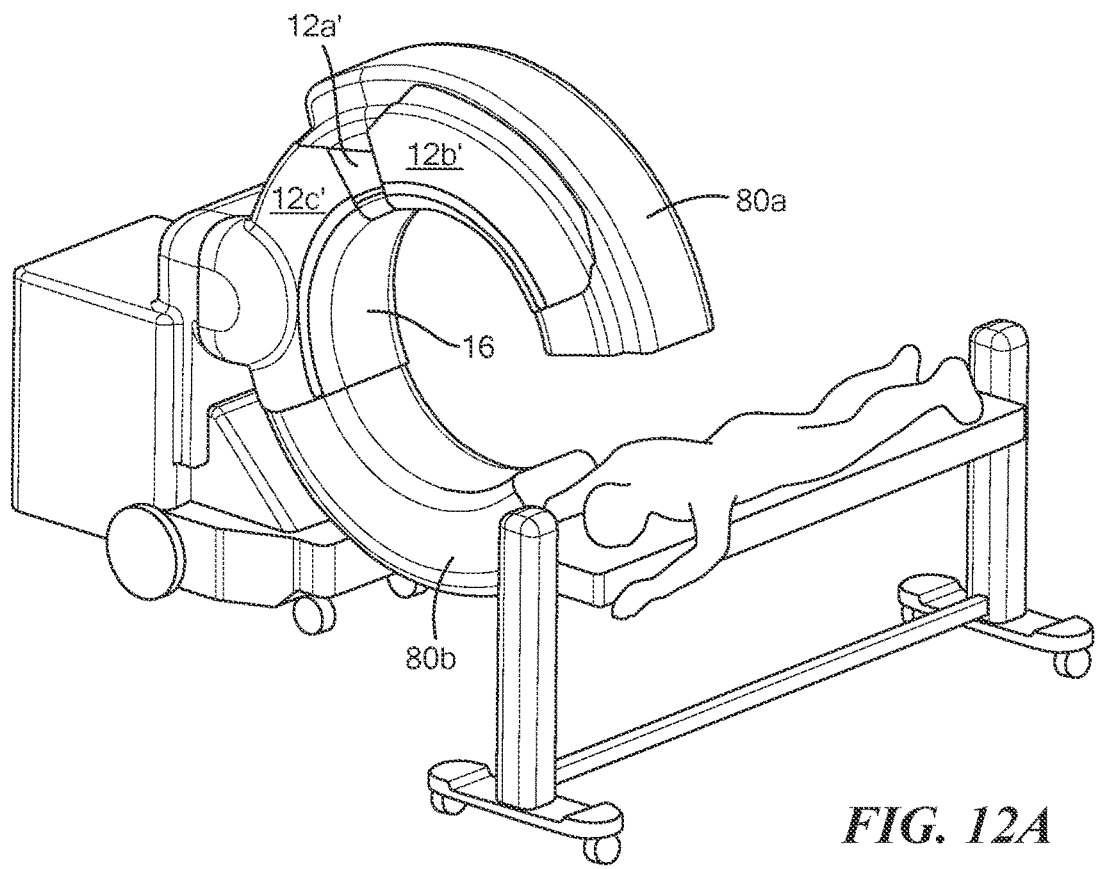
FIGS. 12A-12B show another example of a drape configured for a gantry arm with one section which rotates relative to another section.
Figure 12B:
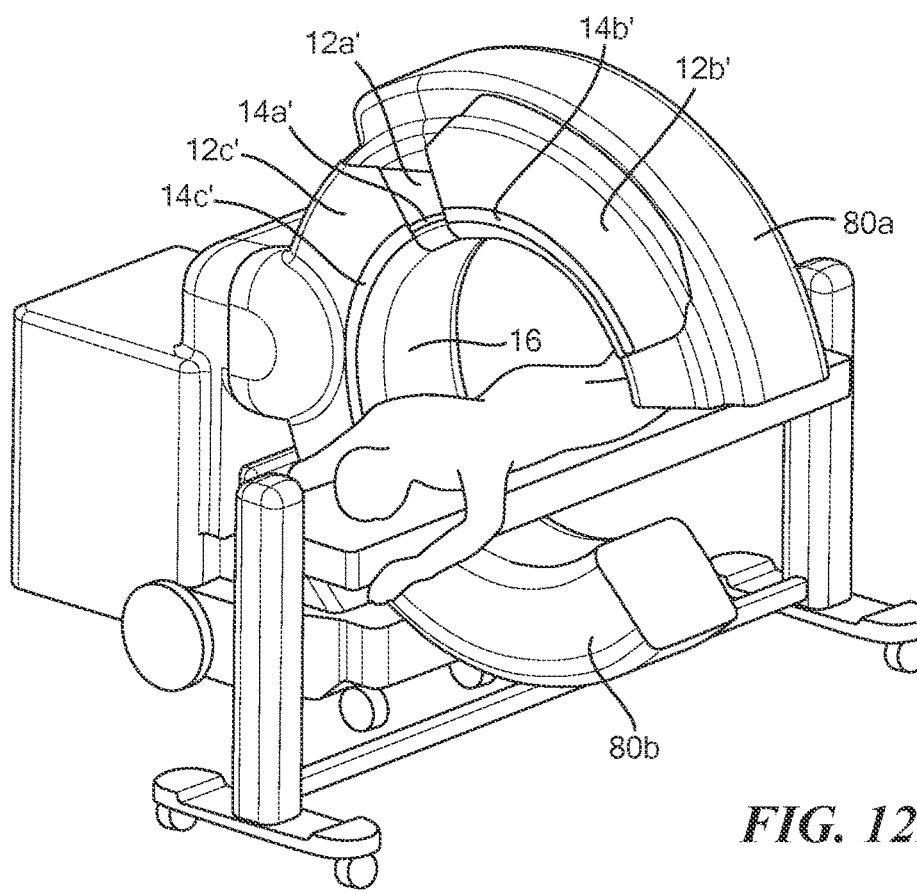
Figure 12C:
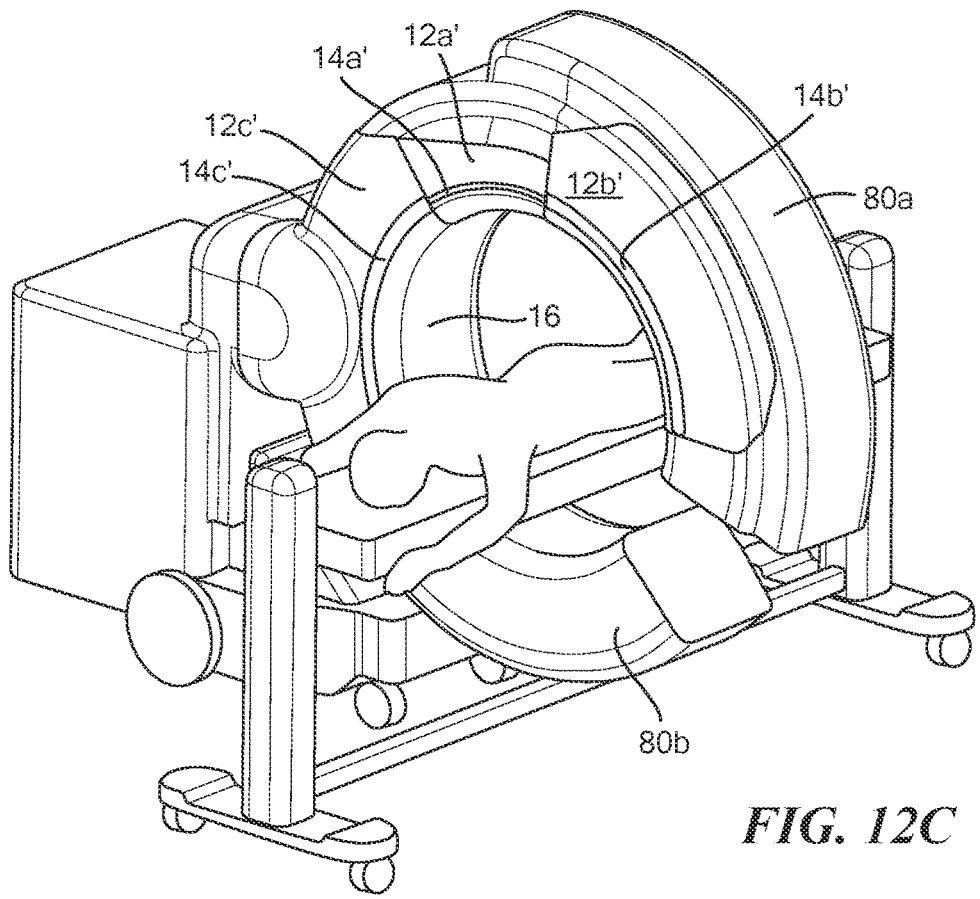
Figure 12D:
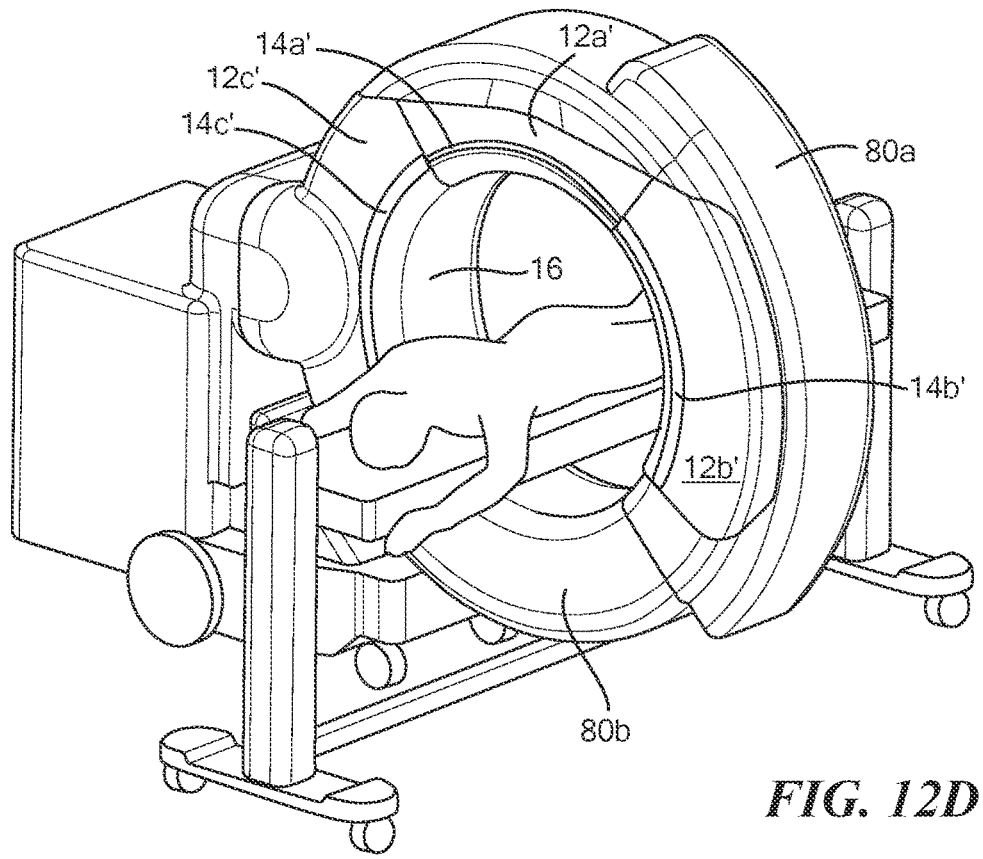
Figure 13:
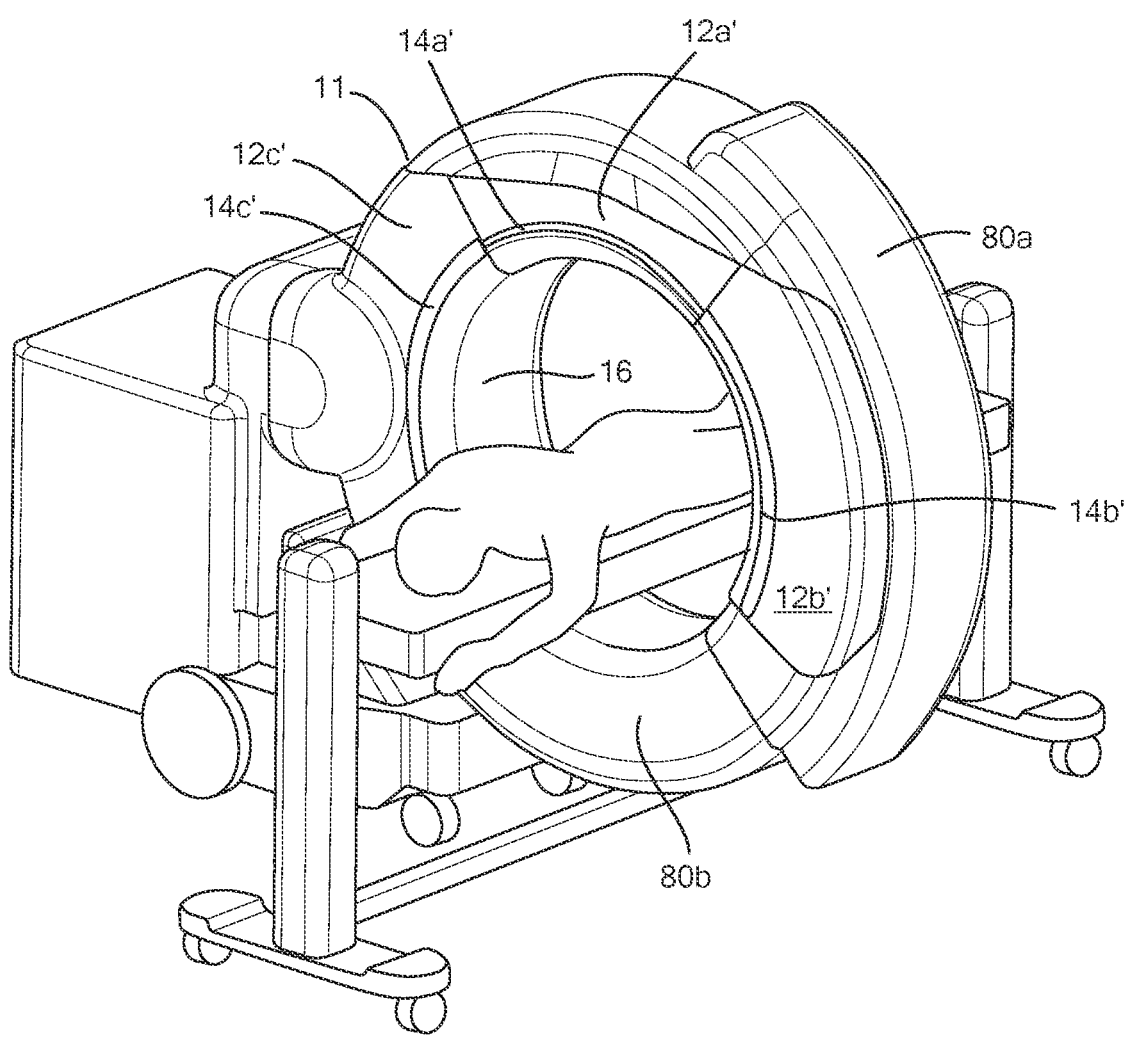
FIGS. 13-14 show a drape with a gantry side wall covering portion formed from adjacent leaves.
Figure 14:
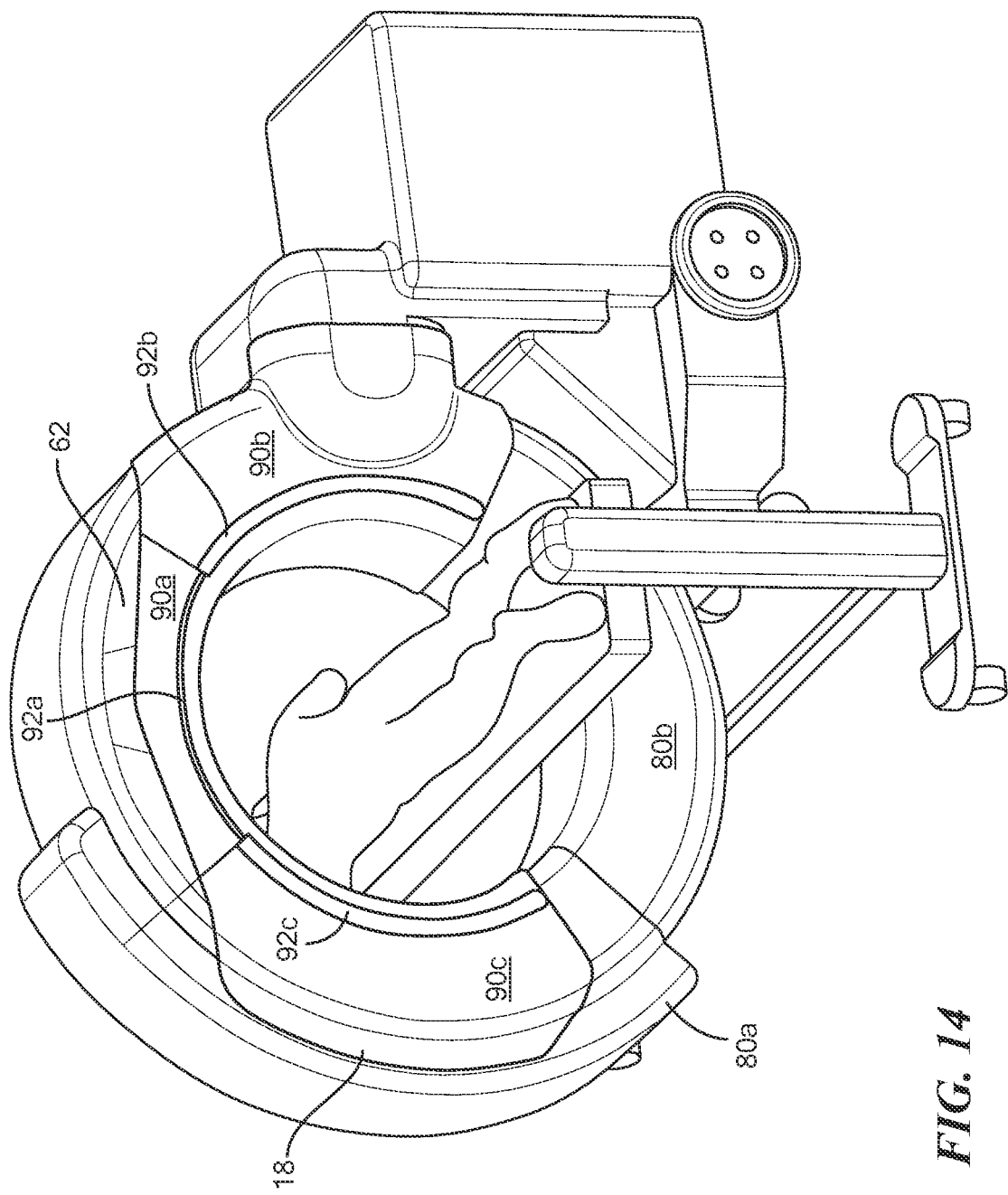
Figure 15:
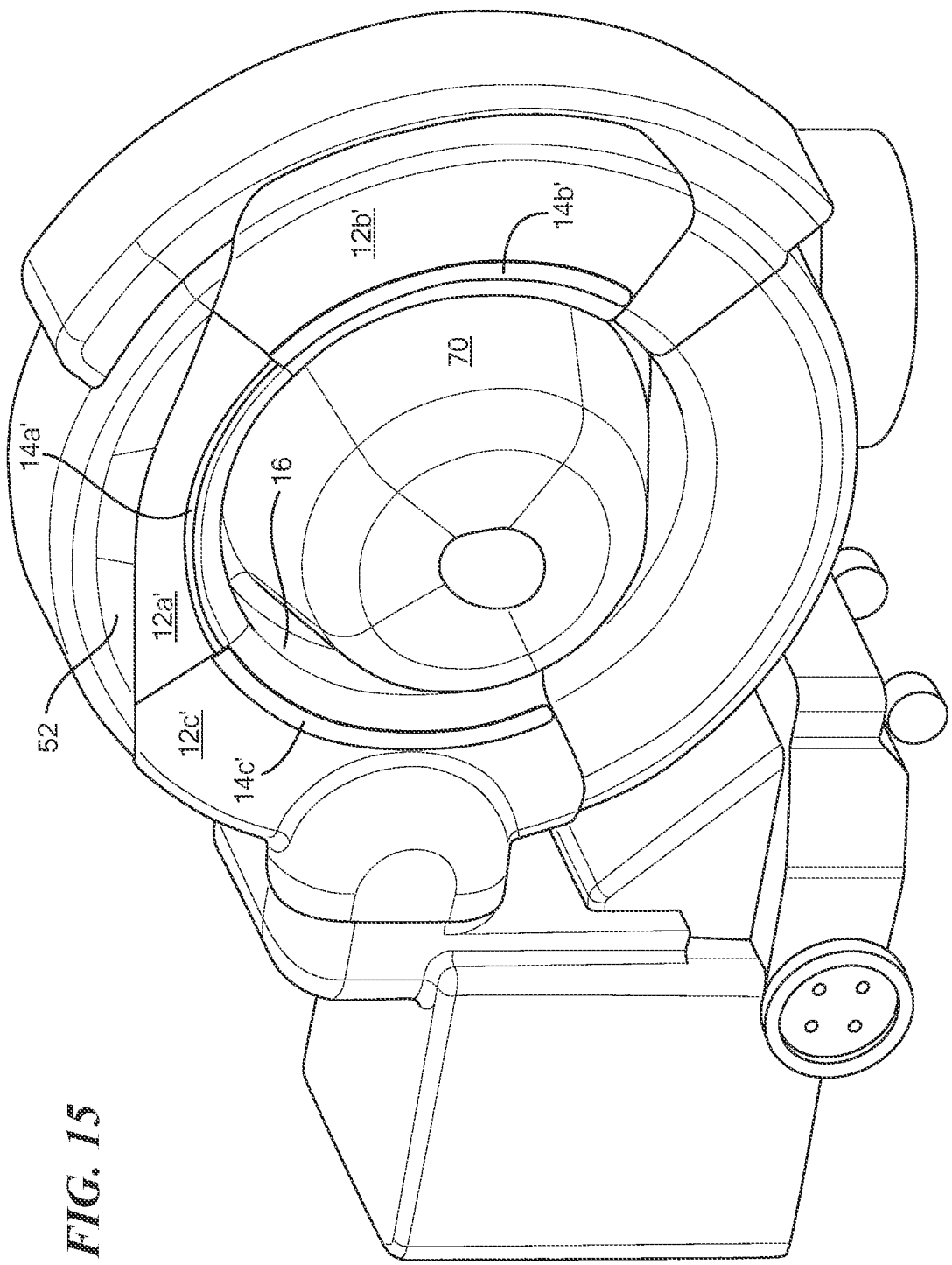
FIGS. 15-16 show an example of a drape with a patient envelope portion.
Figure 16:
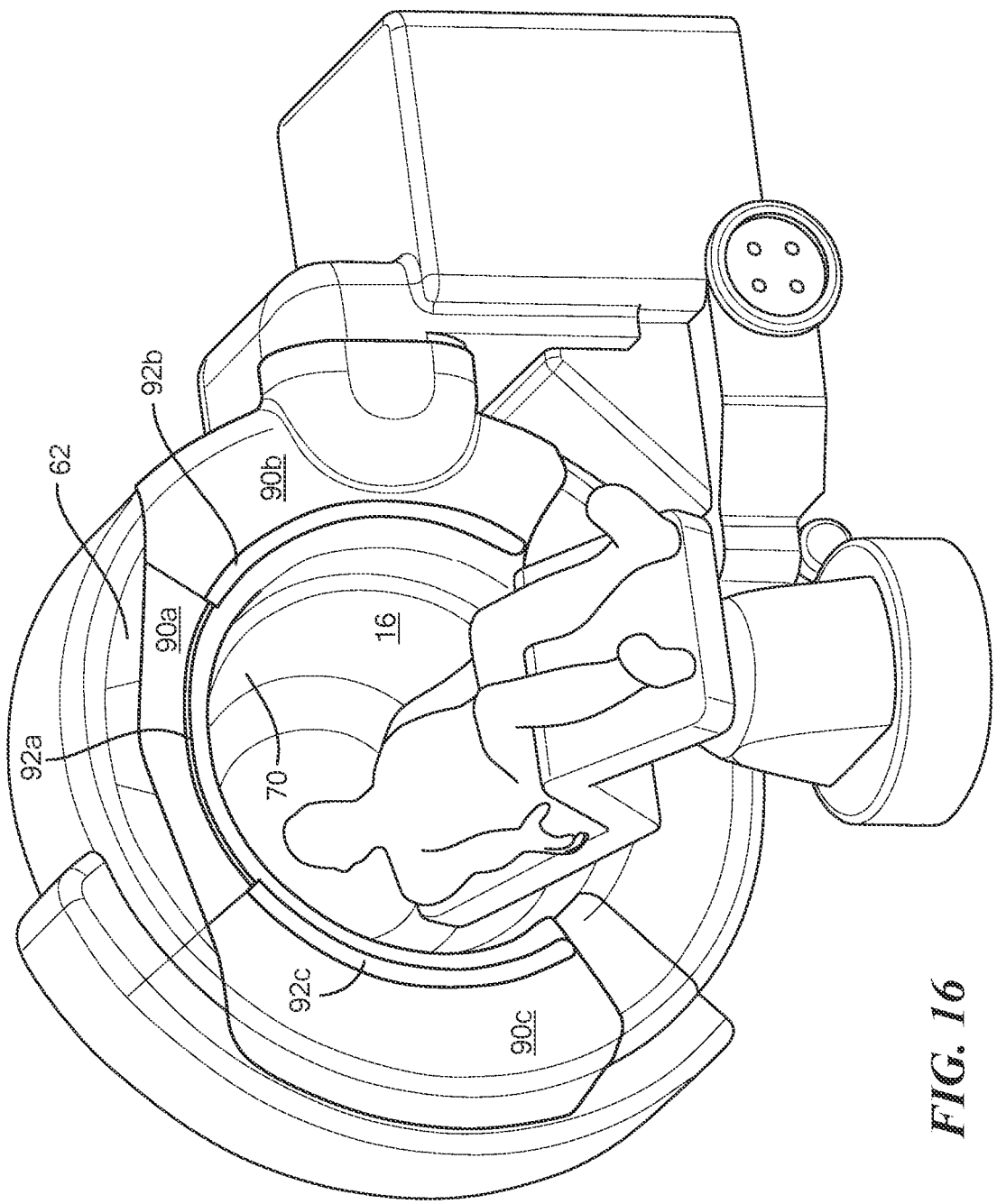

FIGS. 12A-12B depict another drape configured for a gantry arm with section 80*a* which rotates relative to section 80*b*. Leaf portions 12*a*' and 12*c*' of gantry side wall 52 covering portion 11 are affixed to gantry section 80*b*, and leaf portion 12*b*' is affixed to and moves with gantry section 80*a*, and stay 14*b*' telescopes relative to stay 14*a*'. See also FIGS. 13-14 which shows how gantry side wall 62 covering portion 18 also includes leaves 90*a* and 90*b* affixed to gantry section 80*b* and leaf 90*c* affixed to and rotating with gantry section 80*a*. And, gantry side wall 62 covering portion 18 includes stays 92*a*-92*c* for each leaf 90*a*-90*c* with stay 92*c* telescoping relative to stay 92*a*. FIGS. 15-16 show the addition of patient envelope portion 70.

By draping the gantry equipment rather than the patient, the equipment need only be draped once per case whereas the technique of draping the patient has to be redone for each scan and potentially result in accidental contamination. The drape disclosed herein is quick and easy to deploy and thus saves time and money. The subject drape may encourage more interoperative scans. It also allows for an unbroken line of sight to navigation arrays. The subject drape also allows for real time robotic access during fluoroscopy.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. An imaging system drape comprising:
a gantry first outer side wall covering portion including a top leaf and one or more adjacent leaves on opposite sides of the top leaf;
a stay associated with the top leaf and for each of the one or more adjacent leaves, the stays are interconnectable;
a gantry inner wall covering portion extending from the gantry first outer side wall covering portion; and
one or more drape portions attached to the gantry inner wall covering portion and securable to a gantry second outer side wall.

2. The drape of claim 1 in which the stays are hinged to each other.

3. The drape of claim 1 in which the stays telescope relative to each other.

4. The drape of claim 1 further including a member securing the top leaf to an adjacent leaf.

5. The drape of claim 1 in which each stay is bonded to its respective leaf.

6. The drape of claim 1 in which the first outer side wall covering portion, the gantry inner wall covering portion, and the one or more drape portions are made of plastic.

7. The drape of claim 1 in which the one or more drape portions form a gantry second outer side wall covering portion.

8. The drape of claim 1 further including one or more hand sleeves associated with the top leaf and/or one or more adjacent leaves of the gantry first outer side wall covering portion.

9. The drape of claim 1 further including a first fastener associated with the top leaf and/or one or more adjacent leaves and mateable with a second fastener on the gantry first outer side wall.

10. The drape of claim 1 in which the one or more drape portions each include retainers securing the drape to the gantry second outer side wall.

11. The drape of claim 1 further including a patient envelope portion.

12. The drape of claim 1 further including additional leaves to cover additional lower portions of the gantry first outer sidewall.

13. The drape of claim 4 in which said member includes a strap.

14. The drape of claim 7 further including a stay member associated with the gantry second outer side wall covering portion.

15. The drape of claim 7 further including a first fastener associated with the gantry second outer side wall covering portion mateable with a second fastener on the gantry second outer side wall covering portion.

16. The drape of claim 7 further including one or more hand sleeves associated with the gantry second outer side wall covering portion.

17. The drape of claim 11 in which the patient envelope portion extends from the gantry inner wall covering portion outwardly through the gantry.

18. The drape of claim 11 in which the patient envelope portion includes a patient fenestration.

19. The drape of claim 17 in which the patient envelope portion includes a stiffener forming a patient viewing window.

20. A method of securing a drape to an imaging system gantry, the method comprising:
securing a gantry first outer side wall covering portion top leaf with a stay to a top portion of the gantry first outer side wall;
deploying an adjacent leaf also with a stay to cover a gantry first outer side wall lower portion on one side of the top portion;
deploying another adjacent leaf also with a stay to cover a gantry first outer side wall lower portion on an opposite side of the top portion; and
affixing adjacent stays together.

21. The method of claim 20 further including deploying additional leaves to cover additional lower portions of the gantry first outer side wall.

22. The method of claim 20 further including:
deploying a gantry inner wall covering portion which extends from the gantry first outer side wall covering portion; and
attaching one or more drape portions attached to the gantry inner wall covering portion and to a gantry second outer side wall.

23. The method of claim 20 in which the stays are hinged to each other.

24. The method of claim 20 in which the stays telescope relative to each other.

25. The method of claim 22 further including deploying a patient envelope portion.

26. The method of claim 25 in which the patient envelope portion extends from the gantry inner wall covering portion outwardly through the gantry.

27. The drape of claim 18 in which the fenestration is located at a terminal portion of the patient envelope portion.

* * * * *